United States Patent [19]
Fujiwara et al.

[11] Patent Number: 5,627,193
[45] Date of Patent: May 6, 1997

[54] QUINOLINE-4-CARBONYLGUANIDINE DERIVATIVES, PROCESS FOR PRODUCING THE SAME AND PHARMACEUTICAL PREPARATIONS CONTAINING THE COMPOUNDS

[75] Inventors: Junya Fujiwara; Haruki Mori; Hiroyuki Yamashita; Takashi Kitamori; Junko Hosoya; Hitoshi Banno, all of Chiba-ken, Japan

[73] Assignee: Mitsui Toatsu Chemicals, Inc., Tokyo, Japan

[21] Appl. No.: 594,789

[22] Filed: Jan. 31, 1996

[30] Foreign Application Priority Data

Feb. 9, 1995 [JP] Japan .................................. 7-021765

[51] Int. Cl.$^6$ .................................................. A61K 31/47
[52] U.S. Cl. .......................................... 514/311; 546/169
[58] Field of Search ............................. 514/311; 546/169

[56] References Cited

U.S. PATENT DOCUMENTS

| | | | |
|---|---|---|---|
| 4,680,299 | 7/1987 | Hesson | 514/311 |
| 4,684,652 | 8/1987 | Dubroeucq et al. | 514/311 |
| 4,711,890 | 12/1987 | Dubroeucq et al. | 514/311 |
| 4,970,214 | 11/1990 | Murase et al. | 546/169 |
| 5,071,987 | 12/1991 | Raulfs et al. | 546/169 |
| 5,204,329 | 4/1993 | Ackerman et al. | 514/311 |
| 5,373,024 | 12/1994 | Lang et al. | 564/237 |

FOREIGN PATENT DOCUMENTS

| | | | |
|---|---|---|---|
| 0122776 | 9/1984 | European Pat. Off. | 514/311 |
| 0416499 | 3/1991 | European Pat. Off. | 514/311 |
| 0590455 | 4/1994 | European Pat. Off. | 514/311 |
| 0622356 | 11/1994 | European Pat. Off. | 514/311 |
| 0682017 | 11/1995 | European Pat. Off. | 514/311 |
| WO94/26709 | 11/1994 | WIPO | 514/311 |

OTHER PUBLICATIONS

Rex Mahnensmith et al, The Plasma Membrane Sodium--Hydrogen Exchanger and Its Role in Physiological and Pathophysiological Processes, *Circulation Research*, Jun. 1985, vol. 56, No. 6, pp. 773–788.
Dieter Rosskopf et al, Membrane Sodium–Proton Exchange and Primary Hypertension, *Hypertension*, vol. 21, No. 5, May 1993, pp. 608–617.
Steven Dennis et al, Effects of Proton Buffering and of Amiloride Derivatives on Reperfusion Arrhythmias in Isolated Rat Hearts, *Circulation Research*, vol. 66, No. 4, Apr. 1990, pp. 1156–1159.
Masayuki Mitsuka et al, Na$^+$–H$^+$ Exchange Inhibitors Decrease Neointimal Formation After Rat Carotid Injury, *Circulation Research*, vol. 73, No. 2, Aug. 1993, pp. 269–275.
Jun Fukuzawa et al, Supplement I, *Circulation*, vol. 86, No. 4, Oct. 1992, pp. 1–176—1–177.
Martin Schwartz et al, Effect of Cell Spreading on Cytoplasmic pH in Normal and Transformed Fibroblasts, *Proc. Natl. Acad. Sci. USA*, vol. 86, Jun. 1989, pp. 4525–4529.
Sanna Rosengren et al, Migration–associated Volume Changes in Neutrophils Facilitate the Migratory Process in Vitro, *American Journal of Physiol.*, vol. 267, 1994, pp. C1623–C1632.
Thomas Kleyman et al, Amiloride and Its Analogs as Tools in the Study of Ion Transport, *J. Membrane Biol.*, vol. 105, 1988, pp. 1–21.
Dr. H. A. Staab, Syntheses Using Heterocyclic Amides (Azolides), *Angew. Chem. Internat. Edit.*, vol. I, No. 7, 1962, pp. 351–367.
Theodora Greene, *Protective Groups in Organic Synthesis*, 1981, 87–287.
Arnold Weissberger et al, *Quinolines*, Part I, 1977, pp. 124–319.
*Berichte*, 20, pp. 277–280, 1887.
W. Pfitzinger, Chinolinderivate aus Isatinsäure, *J. Prakt. Chem.*, 33, 100, 1886.
A.R. Katritzky et al, *Advances in Heterocyclic Chemistry*, vol. 18, 1975, pp. 1–58.
C.D. Foster et al, Characterization of Na$^+$–H$^+$ Exchange in Segments of Rat Mesenteric Artery, *American Physiological Society*, 262, 31, 1992, pp. H–1651—H1656.
M.J.A. Walker et al, The Lanbeth Conventions: Guidelines for the Study of Arrhythmias in Ischaemia, Infarction, and Reperfusion, *Cardiovascular Research*, vol. 22, 1988 pp. 447–455.

*Primary Examiner*—James H. Reamer
*Attorney, Agent, or Firm*—Burns, Doane, Swecker & Mathis

[57] ABSTRACT

The present invention relates to quinoline-4-carbonylguanidine derivative represented by formula (1)

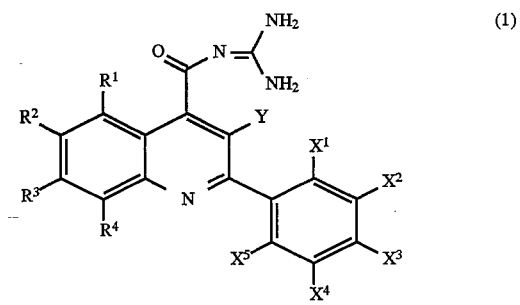

and pharmaceutically acceptable salt thereof, a process for producing the same, and a Na$^+$/H$^+$ exchanger inhibitor containing the compound as an active ingredient. The compounds of the present invention are useful as an agent for treating or preventing various diseases by hyperfunction of the Na$^+$/H$^+$ exchanger and as a diagnostic agent for these diseases.

27 Claims, No Drawings

QUINOLINE-4-CARBONYLGUANIDINE DERIVATIVES, PROCESS FOR PRODUCING THE SAME AND PHARMACEUTICAL PREPARATIONS CONTAINING THE COMPOUNDS

BACKGROUND OF THE INVENTION

1. Field of the Invention

The present invention relates to novel quinoline-4-carbonylguanidine derivatives or pharmaceutically acceptable salts thereof. More specifically, the present invention relates to an agent which contains the above-mentioned compounds and which is particularly useful as an inhibitor of an $Na^+/H^+$ exchanger (hereinafter referred to as "NHE") for treating or preventing hypertension, arrhythmia, myocardial infarction, angina pectoris, arteriosclerosis, diabetic complication, fibrosis of lung, liver, kidney and the like, cell growth of vascular smooth muscle, cardiac muscle, prostate and the like, and cancers, a protective solution of internal organs cut from the body for transplantation or internal organs transplanted, and a diagnostic agent.

2. Description of the Related Art

It has been known that when the pH in cells changes, the activity of enzymes or ion channels in cells also changes, which greatly influences physiological functions of the cells. Accordingly, a mechanism of regulating an intracellular pH has been long studied, and the presence of various ion exchangers that contribute to maintenance of homeostasis of an intracellular pH in cells has been clarified. NHE is one of these systems, and a variety of physiological functions such as regulation of a pH in cells, cell volumes, cell growth and the like have become known. In recent years, it has become clear through experiments that hormones, growth factors and intracellular acidosis activate NHE and result in a cytoplasmic alkalinization [Cir. Res., 57, 773–788 (1985)]. These NHE activators attract attention as factors that cause various diseases, and studies for clarifying the relationship between enhanced NHE activity and these diseases are now assiduously being conducted. With respect to study reports concerning NHE, there are general reports, such as Cir. Res., 57, 773–788 (1985) and Hypertension Hypertension, 21, 607–617 (1993).

Recently, it has been reported that NHE is activated in myocardial ischemia and reperfusion [Cir. Res., 66, 1156–1159 (1990)], and that inhibition of NHE is effective for preventing disorders caused by myocardial ischemia and the consequential arrhythmia [Cir. Res.,73, 269–275, (1993) ]. Accordingly, the NHE inhibitor is useful for preventing or treating angina pectoris and myocardial infarction, ischemic arrhythmia, reperfusion arrhythmia, organ disorders following ischemia and reperfusion, cerebral ischemic disorders, cerebral apoplexy and ischemic diseases of limbs and peripheral organs. Further, it is useful as an agent for myocardial protection and organ protection under anoxic condition and reperfusion state in surgical operation or transplantation of internal organs, or as an ingredient of a protective solution for treating or preventing disorders of internal organs cut from the body for transplantation or internal organs transplanted.

The relationship between NHE activity and hypertension has attracted attention so far. Recently, hyperfunction of NHE has been observed in cells such as platelets, erythrocytes, leukocytes and the like of patients suffering from essential hypertension [Hypertension, 21, 607–617 (1993)], and the relationship between NHE and hypertension has been clarified.

Further, it has been reported that in many cells, NHE participates in cell growth through inclusion of $Na^+$ into cells and intracellular alkalinization, and that amiloride having NHE inhibitory activity suppresses cardiac hypertrophy [Circulation, 86 ( Suppl. I) I -177 (1992)]. That is, it is suggested that the NHE inhibitor is useful as an agent for preventing or treating diseases caused by excessive cell growth with an enhanced NHE activity, such as arteriosclerosis, vascular restenosis after percutaneous transluminal coronary angioplasty (PTCA) associated with a proliferation of vascular smooth muscle cells, rheumatoid arthritis with a proliferation of synovial cells, renal glomerulosclerosis with a proliferation of mesangial cells, pulmonary, hepatic and renal fibrosis with a proliferation of fiblobrasts, diabetic complication caused by vascularization, cardiac hypertrophy, prostatic hypertrophy and the like, and cancers [Cir. Res., 57, 773–788 (1985), Proc. Natl. Acad. Sci. USA., 86, 4525–4529 (1989), and Cir. Res., 73, 269–275 (1993)].

Still further, the relationship between activation of NHE and inflammation has been reported [Am. J. Physiol., 267, C1623–C1632 (1994)], and the NHE inhibitor is useful as an agent for treating or preventing diseases caused by infiltration of leukocytes associated with enhanced NHE activity, such as inflammation.

As stated above, it has been known that NHE activity is enhanced in various states of NHE. The NHE activity can easily be measured by using a strong NHE inhibitor to easily obtainable cells such as platelets, erythrocytes and leukocytes. That is, the NHE inhibitor is also useful as a diagnostic agent for hypertension, diseases caused by cell growth, diabetes and the like.

Amiloride derivatives containing a guanidinocarbonyl group have been used in animal tests as an NHE inhibitor so far. It has been reported that these compounds suppress simultaneously $Na^+$ (sodium ion) channels and an $Na^+/Ca^+$ (sodium ion/calcium ion) exchanger in concentrations in which they suppress NHE, and with respect to the NHE inhibitory activity, $IC_{50}$ (50% inhibitory concentration) is approximately 100 μM which is not satisfactory [J. Membrane, Biol., 105, 1–21 (1988)]. The above-mentioned amiloride derivatives and benzoylguanidine derivatives [JP A 3-106858 (Family: EP416499), and the like; hereinafter "JP A" means Publication of Japanese Patent Application] which are monocyclic compounds have been known as an NHE inhibitor. On the other hand, isoquinoline derivatives [JP A 6-211799 (Family: EP590455)], indole derivatives [JP A 7-10839 (Family: EP622356)] and quinoline derivatives (EP682017) have been known as compounds having a fused ring. The quinoline derivatives described in EP682017 are compounds containing a guanidinocarbonyl group in the 3-position. With respect to the NHE inhibitory activity, $IC_{50}$ is several micromoles, and it is not satisfactory.

The present invention is to provide compounds which have strong NHE inhibitory activity and which are useful as an agent for preventing or treating various diseases caused by hyperfunction of NHE and as a diagnostic agent.

SUMMARY OF THE INVENTION

The present inventors have assiduously conducted investigations to solve the above-mentioned problems, and have consequently found that quinoline-4-carbonylguanidine derivatives having a phenyl group in the 2-position have strong NHE inhibitory activity. This finding has led to the completion of the present invention. That is, the present invention relates to:

[1] A quinoline-4-carbonylguanidine derivative represented by formula (1)

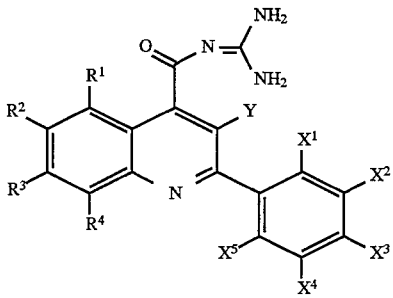

wherein
R¹, R², R³ and R⁴ are the same or different and each represents a hydrogen atom, an alkyl group having from 1 to 6 carbon atoms, a halogen atom, a nitro group, an amino group, a hydroxyl group, an alkyloxy group having from 1 to 6 carbon atoms, an alkyloxy group having from 1 to 6 carbon atoms and containing a terminal alkyloxy group having from 1 to 6 carbon atoms, an alkylsulfonylamino group having from 1 to 6 carbon atoms, or an alkanoylamino group having from 2 to 6 carbon atoms, $X^1$, $X^2$, $X^3$, $X^4$ and $X^5$ are the same or different and each represents a hydrogen atom, an alkyl group having from 1 to 6 carbon atoms, a halogen atom, a nitro group, an amino group, a hydroxyl group, a trifluoromethyl group, an alkyloxy group having from 1 to 6 carbon atoms, an alkyloxy group having from 1 to 6 carbon atoms and containing a terminal alkyloxy group having from 1 to 6 carbon atoms, or a trifluoromethoxy group, and Y represents a hydrogen atom, or an alkyl group having from 1 to 6 carbon atoms,
or a pharmaceutically acceptable salt thereof.

[2] The quinoline-4-carbonylguanidine derivative or the pharmaceutically acceptable salt thereof as mentioned in [1], wherein one or two of R¹, R², R³ and R⁴ represent an alkyloxy group having from 1 to 6 carbon atoms.

[3] The quinoline-4-carbonylguanidine derivative or the pharmaceutically acceptable salt thereof as mentioned in [1], wherein $X^1$ represents a methyl group.

[4] The quinoline-4-carbonylguanidine derivative or the pharmaceutically acceptable salt thereof as mentioned in [2], wherein $X^1$ represents a methyl group.

[5] A process for producing the quinoline-4-carbonylguanidine derivative of [1], [2], [3] or [4], which comprises reacting a quinoline-4-carboxylic acid derivative represented by formula (2)

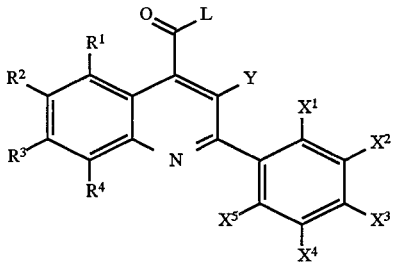

wherein
L represents a hydroxyl group, or a leaving group that can easily be substituted by means of a nucleophilic reagent, and
R¹, R², R³, R⁴, $X^1$, $X^2$, $X^3$, $X^4$, $X^5$ and Y are as defined in formula (1)
with guanidine.

[6] A pharmaceutical composition containing as an active ingredient the quinoline-4-carbonylguanidine derivative or the pharmaceutically acceptable salt thereof as mentioned in [1], [2], [3] or [4].

[7] A $Na^+/H^+$ exchanger inhibitor containing as an active ingredient the quinoline-4-carbonylguanidine derivative or the pharmaceutically acceptable salt thereof as mentioned in [1], [2], [3] or [4].

[8] An agent for treating or preventing hypertension, the agent containing as an active ingredient the quinoline-4-carbonylguanidine derivative or the pharmaceutically acceptable salt thereof as mentioned in [1], [2], [3] or [4].

[9] An agent for treating or preventing arrhythmia, the agent containing as an active ingredient the quinoline-4-carbonylguanidine derivative or the pharmaceutically acceptable salt thereof as mentioned in [1], [2], [3] or [4].

[10] An agent for treating or preventing angina pectoris, reperfusion arrhythmia and myocardial infarction caused by ischemia, ischemic arrhythmia, organ disorders caused by ischemia and reperfusion, cerebral ischemic disorders, cerebral apoplexy and ischemic diseases of limbs and peripheral organs, the agent containing as an active ingredient the quinoline-4-carbonylguanidine derivative or the pharmaceutically acceptable salt thereof as mentioned in [1], [2], [3] or [4].

[11] An agent for treating or preventing diseases caused by cell proliferation or hypertrophy, the agent containing as an active ingredient the quinoline-4-carbonylguanidine derivative or the pharmaceutically acceptable salt thereof as mentioned in [1], [2], [3] or [4].

[12] An agent for treating or preventing organ disorders caused by ischemia in a surgical operation or transplantation of internal organs, the agent containing as an active ingredient the quinoline-4-carbonylguanidine derivative or the pharmaceutically acceptable salt thereof as mentioned in [1], [2], [3] or [4].

[13] An agent for treating or preventing diseases caused by infiltration of leukocytes, the agent containing as an active ingredient the quinoline-4-carbonylguanidine derivative or the pharmaceutically acceptable salt thereof as mentioned in [1], [2], [3] or [4].

[14] A protective solution internal organs cut from the body for transplantation or internal organs transplanted, the protective solution containing as an active ingredient the quinoline-4-carbonylguanidine derivative or the pharmaceutically acceptable salt thereof as mentioned in [1], [2], [3] or [4].

[15] An agent for diagnosis of hypertension, diseases caused by cell growth and diabetes through inhibition of a $Na^+/H^+$ exchanger, said agent containing as an active ingredient the quinoline-4-carbonylguanidine derivative or the pharmaceutically acceptable salt thereof as mentioned in [1], [2], [3] or [4].

DESCRIPTION OF THE PREFERRED EMBODIMENTS

The present invention will be described in detail below.
R¹, R², R³ and R⁴ in formula (1) are explained hereinafter. The alkyl group having from 1 to 6 carbon atoms, as represented by R¹, R², R³ and R⁴, is a linear, branched or cyclic alkyl group having from to 6 carbon atoms. Examples of the alkyl group include methyl, ethyl, n-propyl, n-butyl, n-pentyl, n-hexyl, isopropyl, 2-methylpropyl, 1-methylpropyl, tert-butyl, 2-methylbutyl, 1-methylbutyl, 1,2-dimethylpropyl, 1,1-dimethylpropyl, 2,2-dimethylpropyl, 4-methylpentyl, 3-methylpentyl, 2-methylpentyl, 1-methylpentyl, 1,2,2-trimethylpropyl, 1,1- dimethylbutyl, 1,1,2-trimethylpropyl, 2,2-dimethylbutyl, 1,3-dimethylbutyl, 2,3-dimethylbutyl, cyclopropyl, cyclobutyl, cyclopentyl and cyclohexyl groups.

Examples of the halogen atom include iodine, bromine, chlorine and fluorine atoms.

The alkyloxy group having from 1 to 6 carbon atoms is a linear, branched or cyclic alkyloxy group having from 1 to 6 carbon atoms. Examples of the alkyloxy group include methoxy, ethoxy, n-propyloxy, n-butyloxy, n-pentyloxy, n-hexyloxy, isopropyloxy, 2-methylpropyloxy, 1-methylpropyloxy, tert-butyloxy, 2-methylbutyloxy, 1-methylbutyloxy, 1,2-dimethylpropyloxy, 1,1-dimethylpropyloxy, 2,2-dimethylpropyloxy, 4-methylpentyloxy, 3-methylpentyloxy, 2-methylpentyloxy, 1-methylpentyloxy, 1,2,2-trimethylpropyloxy, 1,1-dimethylbutyloxy, 1,1,2-trimethylpropyloxy, 2,2-dimethylbutyloxy, 1,3-dimethylbutyloxy, 2,3-dimethylbutyloxy, cyclopropyloxy, cyclobutyloxy, cyclopentyloxy and cyclohexyloxy groups.

The alkyloxy group having from 1 to 6 carbon atoms and containing a terminal alkyloxy group having from 1 to 6 carbon atoms include methoxymethyloxy, ethoxymethyloxy, n-propyloxyethyloxy, isopropyloxypropyloxy, cyclopropyloxybutyloxy, n-butyloxypentyloxy, tert-butyloxyhexyloxy, 2-methylpropyloxymethyloxy, 1-methyloxyethyloxy, n-pentyloxypropyloxy, cyclopentyloxymethyloxy, n-hexyloxybutyloxy and cyclohexyloxypentyloxy groups.

Examples of the alkylsulfonylamino group having from 1 to 6 carbon atoms include methanesulfonylamino, ethanesulfonylamino, n-propanesulfonylamino, n-butanesulfonylamino, n-pentanesulfonylamino, n-hexanesulfonylamino, isopropanesulfonylamino, 2-methylpropanesulfonylamino, 1-methylpropanesulfonylamino, tert-butanesulfonylamino, 3-methylbutanesulfonylamino, 2-methylbutanesulfonylamino, 1-methylbutanesulfonylamino, 1,2-dimethylpropanesulfonylamino, 1,1-dimethylpropanesulfonylamino, 2,2-dimethylpropanesulfonylamino, 4-methylpentanesulfonylamino, 3-methylpentanesulfonylamino, 2-methylpentanesulfonylamino, 1-methylpentanesulfonylamino, 1,2,2-trimethylpropanesulfonylamino, 1,1-dimethylbutanesulfonylamino, 1,1,2-trimethylpropanesulfonylamino, 2,2-dimethylbutanesulfonylamino, 1,3-dimethylbutanesulfonylamino, 2,3-dimethylbutanesulfonylamino, cyclopropanesulfonylamino, cyclobutanesulfonylamino, cyclopentanesulfonylamino and cyclohexanesulfonylamino groups.

Examples of the alkanoylamino group having from 2 to 6 carbon atoms include acetylamino, propionylamino, butyrylamino, valerylamino, hexanoylamino, isobutyrylamino, isovalerylamino, pivaloylamino and cyclopentylcarbonylamino groups.

One or two of $R^1$, $R^2$, $R^3$ and $R^4$ are preferably an alkyloxy group having from 1 to 6 carbon atoms.

$X^1$, $X^2$, $X^3$, $X^4$ and $X^5$ in formula (1) are explained hereinafter. The alkyl group having from 1 to 6 carbon atoms, as represented by $X^1$, $X^2$, $X^3$, $X^4$ and $X^5$, is a linear, branched or cyclic alkyl group having from 1 to 6 carbon atoms. Examples of the alkyl group include methyl, ethyl, n-propyl, n-butyl, n-pentyl, n-hexyl, isopropyl, 2-methylpropyl, 1-methylpropyl, tert-butyl, 2-methylbutyl, 1-methylbutyl, 1,2-dimethylpropyl, 1,1-dimethylpropyl, 2,2-dimethylpropyl, 4-methylpentyl, 3-methylpentyl, 2-methylpentyl, 1-methylpentyl, 1,2,2-trimethylpropyl, 1,1-dimethylbutyl, 1,1,2-trimethylpropyl, 2,2-dimethylbutyl, 1,3-dimethylbutyl, 2,3-dimethylbutyl, cyclopropyl, cyclobutyl, cyclopentyl and cyclohexyl groups.

Examples of the halogen atom include iodine, bromine, chlorine and fluorine atoms.

The alkyloxy group having from 1 to 6 carbon atoms is a linear, branched or cyclic alkyloxy group having from 1 to 6 carbon atoms. Examples of the alkyloxy group include methoxy, ethoxy, n-propyloxy, n-butyloxy, n-pentyloxy, n-hexyloxy, isopropyloxy, 2-methylpropyloxy, 1-methylpropyloxy, tert-butyloxy, 2-methylbutyloxy, 1-methylbutyloxy, 1,2-dimethylpropyloxy, 1,1-dimethylpropyloxy, 2,2-dimethylpropyloxy, 4-methylpentyloxy, 3-methylpentyloxy, 2-methylpentyloxy, 1-methylpentyloxy, 1,2,2-trimethylpropyloxy, 1,1-dimethylbutyloxy, 1,1,2-trimethylpropyloxy, 2,2-dimethylbutyloxy, 1,3-dimethylbutyloxy, 2,3-dimethylbutyloxy, cyclopropyloxy, cyclobutyloxy, cyclopentyloxy and cyclohexyloxy groups.

The alkyloxy group having from 1 to 6 carbon atoms and containing a terminal alkyloxy group having from 1 to 6 carbon atoms include methoxymethyloxy, ethoxymethyloxy, n-propyloxyethyloxy, isopropyloxypropyloxy, cyclopropyloxybutyloxy, n-butyloxypentyloxy, tert-butyloxyhexyloxy, 2-methylpropyloxymethyloxy, 1-methyloxyethyloxy, n-pentyloxypropyloxy, cyclopentyloxymethyloxy, n-hexyloxybutyloxy and cyclohexyloxypentyloxy groups.

$X^1$ is preferably a methyl group.

In formula (1), the alkyl group having from 1 to 6 carbon atoms is a linear, branched or cyclic alkyl group having from 1 to 6 carbon atoms. Examples of the alkyl group include methyl, ethyl, n-propyl, n-butyl, n-pentyl, n-hexyl, isopropyl, 2-methylpropyl, 1-methylpropyl, tert-butyl, 2-methylbutyl, 1-methylbutyl, 1,2-dimethylpropyl, 1,1-dimethylpropyl, 2,2-dimethylpropyl, 4-methylpentyl, 3-methylpentyl, 2-methylpentyl, 1-methylpentyl, 1,2,2-trimethylpropyl, 1,1-dimethylbutyl, 1,1,2-trimethylpropyl, 2,2-dimethylbutyl, 1,3-dimethylbutyl, 2,3-dimethylbutyl, cyclopropyl, cyclobutyl, cyclopentyl and cyclohexyl groups.

When $R^1$, $R^2$, $R^3$, $R^4$, $X^1$, $X^2$, $X^3$, $X^4$, $X^5$ or Y contains an asymmetric carbon atom in formula (1), the compounds of formula (1) in the present invention include optically active compounds.

The compounds of formula (1) can be formed into pharmaceutically acceptable salts as required. Examples of the salts include salts with inorganic acids such as hydrochloric acid, hydrobromic acid, phosphoric acid and sulfuric acid or organic acids such as formic acid, acetic acid, fumaric acid, citric acid, maleic acid, oxalic acid, malic acid, tartaric acid, methanesulfonic acid, benzenesulfonic acid and p-toluenesulfonic acid.

A process for producing the compounds of the present invention will be described in detail below.

The compounds of the present invention can be produced by mixing quinoline-4-carboxylic acid derivatives represented by formula (2)

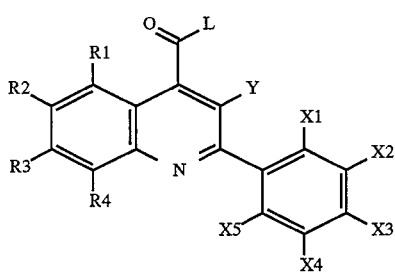

wherein

L represents a hydroxyl group or a leaving group that can easily be substituted by means of a nucleophilic reagent, and $R^1$, $R^2$, $R^3$, $R^4$, $X^1$, $X^2$, $X^3$, $X^4$, $X^5$ and Y are as defined in formula (1)

with guanidine in the absence of a solvent or dissolving or suspending the same in an appropriate solvent or dispersing agent, and reacting the mixture. The ratio of the compounds of formula (2) and guanidine is not particularly limited. The molar ratio of the former: the latter is usually between 1:1 and 1:20, preferably between 1:3 and 1:10. The compounds obtained by this reaction can be purified by an ordinary method such as recrystallization, silica-gel column chromatography or the like.

The reaction will be explained when L is a hydroxyl group and when L is a group other than a hydroxyl group.

(1) L is a hydroxyl group:

A condensation agent can be used in the reaction. Appropriate examples of the solvent or the dispersing agent used in this reaction include benzene, toluene, xylene, 1,4-dioxane, dimethylformamide (hereinafter referred to as "DMF"), tetrahydrofuran (hereinafter referred to as "THF"), ethyl ether, 1,2-dimethoxyethane, dimethylsulfoxide (hereinafter referred to as "DMSO"), chloroform, dichloromethane, and 1,2-dichloroethane.

Examples of the condensation agent which can be used in the reaction include 1,1'-carbonyldiimidazole [H. A. Staab, Angew. Chem. Int. Ed. Engl., 1, 351–367, (1962)], dicyclohexylcarbodiimide (hereinafter referred to as "DCC"), 1-ethyl-3-(3'-dimethylaminopropyl)carbodiimide, and diphenylphosphorylazide.

The reaction is conducted at a temperature ranging from −20° C. to a reflux temperature of the reaction mixture, for example, from −10° to 150° C., preferably from room temperature to 100° C. The reaction time varies with conditions, and it is between approximately 1 and 48 hours.

(2) L is a group other than a hydroxyl group:

The active compounds of the quinoline-4-carboxylic acid derivatives represented by formula (2) include acid halides (L=halogen), acid anhydrides (especially mixed acid anhydrides—L=alkoxycarbonyloxy), and carboxylate esters. These can easily be formed from carboxylic acids (L=OH) of formula (2) by a known method.

As an acid halide, carbonyl chloride can be formed from a carboxylic acid using a chlorination agent such as thionyl chloride, oxalyl chloride, phosphorus pentachloride or the like.

An acid anhydride can be formed from a carboxylic acid using monoalkyl carbonate such as ethyl chlorocarbonate and base such as triethylamine.

As a carboxylate ester, a methyl ester can be formed by, for example, treating a carboxylic acid with a hydrogen chloride gas in methanol, and p-nitrophenyl ester which is an active ester can be formed by treating p-nitrophenol with DCC.

Appropriate examples of the solvent or the dispersing agent which is used in the reaction of the carboxylic acid active compounds and guanidine include methyl ethyl ketone, 1,4-dioxane, DMF, THF, ethyl ether, 1,2-dimethoxyethane, dimethyl sulfoxide, benzene, xylene, toluene, chloroform, dichloromethane, 1,2-dichloroethane, and pyridine. Alcohols such as methanol, ethanol and isopropanol can be used as required.

The reaction of the quinoline-4-carboxylic acid active compounds and guanidine is conducted at a temperature ranging from −20° C. to a reflux temperature of the reaction mixture, for example, from −10° to 150° C., preferably from 0° to 100° C. The reaction time varies with conditions. It is between approximately 1 and 48 hours. Examples of the base that accelerates this reaction include organic bases such as pyridine, dimethylaminopyridine, triethylamine, and diisopropylethylamine; and inorganic bases such as potassium carbonate, sodium carbonate, sodium hydroxide, and potassium hydroxide.

When the quinoline-4-carboxylic acid (L=OH) of formula (2) contains an active group such as a hydroxyl group or an amino group, the active group is protected in advance with a protective group, and deprotection is conducted after the production of quinoline-4-carbonylguanidine by the above-mentioned process, whereby the final quinoline-4-carbonylguanidine derivatives of formula (1) can be obtained. At this time, the protection and the deprotection can be conducted by a known method [for example, T. W. Green: Protective Groups in Organic Synthesis, John Wiley & Sons (1981)].

When the quinoline-4-carbonylguanidine derivatives of formula (1) contain an amino group, these compounds can be produced by reducing quinoline-4-carbonylguanidine derivatives containing a nitro group in a known manner. The reduction is conducted under acidic conditions using a metal such as iron, zinc or the like, or through catalytic hydrogenation in the presence of a catalyst such as palladium on activated carbon (hereinafter referred to as "Pd/C").

A method of producing quinoline-4-carboxylic acid (L=OH) of formula (2) is described in, for example, G. Jones, The Chemistry of Heterocyclic Compounds, vol. 32, Quinolines Part I, John Wiley & Sons. It can be produced by the method of Doebner [Ber., 20, 277 (1887), etc.] or the method of Pfitzinger [J. Prakt. Chem., 33, 100 (1866), etc.]. In the method of Doebner, the reaction of aniline derivatives, benzaldehyde derivatives and pyruvic acid is conducted. In the method Pfitzinger, acetophenone is reacted with isatin derivatives. A method of producing isatin derivatives is described in, for example, F. D. Popp, The Chemistry of Isatin, Adv. Heterocycl. Chem., 18, 1–58 (1975).

The compounds of formula (1) in the present invention is used in a pharmaceutical composition which is effective as an agent for treating or preventing hypertension and arrhythmia caused by activation of NHE, diseases following ischemia which is a primary or secondary cause, diseases caused by cell proliferation or hypertrophy, and diseases caused by infiltration of leukocytes.

Acute or chronic diseases caused by ischemia against which the compounds of the present invention are effective are, for example, angina pectoris, myocardial infarction, ischemic arrhythmia, reperfusion arrhythmia, organ disorders following ischemia and reperfusion, cerebral ischemic disorders, cerebral apoplexy, and ischemic diseases of limbs and peripheral internal organs. The compounds of the present invention can be used as an agent for treating or preventing organ disorders caused by ischemia and reperfusion in surgical operation or transplantation of internal organs, or as an agent for preventing or treating disorders of internal organs cut from the body for transplantation or internal organs transplanted.

Diseases caused by cell proliferation or hypertrophy against which the compounds of the present invention are effective are, for example, arteriosclerosis, vascular restenosis caused by proliferation of a vascular smooth muscle after percutaneous transluminal coronary angioplasty (PTCA), rheumatoid arthritis caused by growth of synovial cells, diabetic complication caused by vascularization, renal glomerulosclerosis caused by growth of mesangial cells, fibrosis of lung, liver, kidney and the like caused by growth of fibroblasts, cardiac hypertrophy, prostatic hypertrophy and cancers.

Diseases caused by infiltration of leukocytes associated with enhanced NHE activity against which the compounds of the present invention are effective are inflammation and the like.

As mentioned above, it is known that NHE activity is enhanced in various diseased states.

The NHE activity can easily be measured by using the compounds of the present invention being strong NHE inhibitors in cells such as platelets, erythrocytes and leukocytes which are easily obtainable. That is, the compounds of the present invention can be used as a diagnostic agent for hypertension, diseases caused by cell growth, diabetes and the like.

Specific examples of the compounds represented by formula (1) in the present invention are shown below. However, the present invention is not limited thereto.

1. 2-phenylquinoline-4-carbonylguanidine
2. 2-(2'-methylphenyl)quinoline-4-carbonylguanidine
3. 2-(2'-ethylphenyl)quinoline-4-carbonylguanidine
4. 2-(2'-n-propylphenyl)quinoline-4-carbonylguanidine
5. 2-(2'-isopropylphenyl)quinoline-4-carbonylguanidine
6. 2-(2'-n-butylphenyl)quinoline-4-carbonylguanidine
7. 2-(2'-cyclobutylphenyl)quinoline-4-carbonylguanidine
8. 2-{2'-(2-methylpropyl)phenyl}quinoline-4-carbonylguanidine
9. 2-{2'-(1-methylpropyl)phenyl}quinoline-4-carbonylguanidine
10. 2-{2'-(1,1-dimethylpropyl)phenyl}quinoline-4-carbonylguanidine
11. 2-{2'-(1,2-dimethylpropyl)phenyl}quinoline-4-carbonylguanidine
12. 2-{2'-(2,2-dimethylpropyl)phenyl}quinoline-4-carbonylguanidine
13. 2-(2'-n-pentylphenyl)quinoline-4-carbonylguanidine
14. 2-(2'-cyclopentylphenyl)quinoline-4-carbonylguanidine
15. 2-{2'-(1-methylbutyl)phenyl}quinoline-4-carbonylguanidine
16. 2-(2'-n-hexylphenyl)quinoline-4-carbonylguanidine
17. 2-{2'-(3-methylpentyl)}phenylquinoline-4-carbonylguanidine
18. 2-{2'-(1,3-dimethylbutyl)phenyl}quinoline-4-carbonylguanidine
19. 2-(3'-methylphenyl)quinoline-4-carbonylguanidine
20. 2-(3'-cyclopropylphenyl)quinoline-4-carbonylguanidine
21. 2-(3'-isopropylphenyl)quinoline-4-carbonylguanidine
22. 2-{3'-(3-methylbutyl)phenyl}quinoline-4-carbonylguanidine
23. 2-(3'-cyclohexylphenyl)quinoline-4-carbonylguanidine
24. 2-{3'-(2-methylpentyl)phenyl}quinoline-4-carbonylguanidine
25. 2-{3'-(1,2,2-trimethylpropyl)phenyl}quinoline-4-carbonylguanidine
26. 2-{3'-(1,1,2-trimethylpropyl)phenyl}quinoline-4-carbonylguanidine
27. 2-{3'-(1,1-dimethylbutyl)phenyl}quinoline-4-carbonylguanidine
28. 2-(4'-methylphenyl)quinoline-4-carbonylguanidine
29. 2-(4'-tert-butylphenyl)quinoline-4-carbonylguanidine
30. 2-{4'-(2-methylbutyl)phenyl}quinoline-4-carbonylguanidine
31. 2-{4'-(2,2-dimethylbutyl)phenyl}quinoline-4-carbonylguanidine
32. 2-{4'-(2,3-dimethylbutyl)phenyl}quinoline-4-carbonylguanidine
33. 2-{4'-(4-methylpentyl)phenyl}quinoline-4-carbonylguanidine
34. 2-{4'-(1-methylpentyl)phenyl}quinoline-4-carbonylguanidine
35. 2-(2',3'-dimethylphenyl)quinoline-4-carbonylguanidine
36. 2-(2',4'-dimethylphenyl)quinoline-4-carbonylguanidine
37. 2-(2',5'-dimethylphenyl)quinoline-4-carbonylguanidine
38. 2-(2',6'-dimethylphenyl)quinoline-4-carbonylguanidine
39. 2-(3',4'-dimethylphenyl)quinoline-4-carbonylguanidine
40. 2-(3',5'-dimethylphenyl)quinoline-4-carbonylguanidine
41. 2-(2',4',6'-trimethylphenyl)quinoline-4-carbonylguanidine
42. 2-(2'-chlorophenyl)quinoline-4-carbonylguanidine
43. 2-(3'-chlorophenyl)quinoline-4-carbonylguanidine
44. 2-(4'-bromophenyl)quinoline-4-carbonylguanidine
45. 2-(4'-iodophenyl)quinoline-4-carbonylguanidine
46. 2-(3'-fluorophenyl)quinoline-4-carbonylguanidine
47. 2-(4'-fluorophenyl)quinoline-4-carbonylguanidine
48. 2-(2'-nitrophenyl)quinoline-4-carbonylguanidine
49. 2-(3'-nitrophenyl)quinoline-4-carbonylguanidine
50. 2-(4'-nitrophenyl)quinoline-4-carbonylguanidine
51. 2-(2'-aminophenyl)quinoline-4-carbonylguanidine
52. 2-(3'-aminophenyl)quinoline-4-carbonylguanidine
53. 2-(4'-aminophenyl)quinoline-4-carbonylguanidine
54. 2-(2'-hydroxyphenyl)quinoline-4-carbonylguanidine
55. 2-(3'-hydroxyphenyl)quinoline-4-carbonylguanidine
56. 2-(4'-hydroxyphenyl)quinoline-4-carbonylguanidine
57. 2-(2'-trifluoromethylphenyl)quinoline-4-carbonylguanidine
58. 2-(3'-trifluoromethylphenyl)quinoline-4-carbonylguanidine
59. 2-(4'-trifluoromethylphenyl)quinoline-4-carbonylguanidine
60. 2-(2'-trifluoromethoxyphenyl)quinoline-4-carbonylguanidine
61. 2-(3'-trifluoromethoxyphenyl)quinoline-4-carbonylguanidine
62. 2-(4'-trifluoromethoxyphenyl)quinoline-4-carbonylguanidine
63. 2-(2'-methoxyphenyl)quinoline-4-carbonylguanidine
64. 2-(3'-methoxyphenyl)quinoline-4-carbonylguanidine
65. 2-(4'-methoxyphenyl)quinoline-4-carbonylguanidine
66. 2-(2'-ethoxyphenyl)quinoline-4-carbonylguanidine
67. 2-(2'-n-propyloxyphenyl)quinoline-4-carbonylguanidine
68. 2-(2'-isopropyloxyphenyl)quinoline-4-carbonylguanidine
69. 2-(2'-n-butyloxyphenyl)quinoline-4-carbonylguanidine 70. 2-(2'-cyclobutyloxyphenyl)quinoline-4-carbonylguanidine
71. 2-{2'-(2-methylpropyloxy)phenyl)}quinoline-4-carbonylguanidine
72. 2-{2'-(1-methylpropyloxy)phenyl)}quinoline-4-carbonylguanidine
73. 2-{2'-(1,1-dimethylpropyloxy)phenyl)}quinoline-4-carbonylguanidine
74. 2-{2'-(1,2-dimethylpropyloxy)phenyl)}quinoline-4-carbonylguanidine
75. 2-{2'-(2,2-dimethylpropyloxy)phenyl)}quinoline-4-carbonylguanidine
76. 2-(2'-n-pentyloxyphenyl)quinoline-4-carbonylguanidine
77. 2-(2'-cyclopentyloxyphenyl)quinoline-4-carbonylguanidine
78. 2-{2'-(1-methylbutyloxy)phenyl)}quinoline-4-carbonylguanidine
79. 2-(2'-n-hexyloxyphenyl)quinoline-4-carbonylguanidine
80. 2-{2'-(3-methylpentyloxy)phenyl}quinoline-4-carbonylguanidine
81. 2-{2'-(1,3-dimethylbutyloxy)phenyl}quinoline-4-carbonylguanidine
82. 2-(3'-cyclopropyloxyphenyl)quinoline-4-carbonylguanidine
83. 2-(3'-isopropyloxyphenyl)quinoline-4-carbonylguanidine
84. 2-(3'-tert-butyloxyphenyl)quinoline-4-carbonylguanidine
85. 2-{3'-(3-methylbutyloxy)phenyl}quinoline-4-carbonylguanidine
86. 2-(3'-cyclohexyloxyphenyl)quinoline-4-carbonylguanidine
87. 2-{3'-(2-methylpentyloxy)phenyl}quinoline-4-carbonylguanidine
88. 2-{3'-(1,2,2-trimethylpropyloxy)phenyl}quinoline-4-carbonylguanidine
89. 2-{3'-(1,1,2-trimethylpropyloxy)phenyl}quinoline-4-carbonylguanidine
90. 2-{3'-(1,1-dimethylbutyloxy)phenyl}quinoline-4-carbonylguanidine
91. 2-{4'-(2-methylbutyloxy)phenyl}quinoline-4-carbonylguanidine
92. 2-{4'-(2,2-dimethylbutyloxy)phenyl}quinoline-4-carbonylguanidine
93. 2-{4'-(2,3-dimethylbutyloxy)phenyl}quinoline-4-carbonylguanidine
94. 2-{4'-(4-methylpentyloxy)phenyl}quinoline-4-carbonylguanidine
95. 2-{4'-(1-methylpentyloxy)phenyl}quinoline-4-carbonylguanidine
96. 2-(2',3'-dimethoxyphenyl)quinoline-4-carbonylguanidine
97. 2-(2',4'-dimethoxyphenyl)quinoline-4-carbonylguanidine
98. 2-(2',5'-dimethoxyphenyl)quinoline-4-carbonylguanidine
99. 2-(2',6'-dimethoxyphenyl)quinoline-4-carbonylguanidine
100. 2-(3',4'-dimethoxyphenyl)quinoline-4-carbonylguanidine
101. 2-(3',5'-dimethoxyphenyl)quinoline-4-carbonylguanidine
102. 2-(2'-methoxymethyloxyphenyl)quinoline-4-carbonylguanidine
103. 2-(3'-ethoxymethyloxyphenyl)quinoline-4-carbonylguanidine
104. 2-(4'-n-propyloxyethyloxyphenyl)quinoline-4-carbonylguanidine
105. 2-(2'-isopropyloxypropyloxyphenyl)quinoline-4-carbonylguanidine
106. 2-(3'-cyclopropyloxybutyloxyphenyl)quinoline-4-carbonylguanidine
107. 2-(4'-n-butyloxypentyloxyphenyl)quinoline-4-carbonylguanidine
108. 2-(2'-tert-butyloxyhexyloxyphenyl)quinoline-4-carbonylguanidine
109. 2-(3'-(2-methylpropyloxymethyloxy)phenyl)quinoline-4-carbonylguanidine
110. 2-{4'-(1-methylpropyloxyethyloxy)phenyl)}quinoline-4-carbonylguanidine
111. 2-(2'-n-pentyloxypropyloxyphenyl)quinoline-4-carbonylguanidine
112. 2-(3'-cyclopentyloxymethyloxyphenyl)quinoline-4-carbonylguanidine
113. 2-(4'-n-hexyloxypentyloxyphenyl)quinoline-4-carbonylguanidine
114. 2-phenyl-3-methylquinoline-4-carbonylguanidine
115. 2-(2'-methylphenyl)-3-methylquinoline-4-carbonylguanidine
116. 2-phenyl-3-ethylquinoline-4-carbonylguanidine
117. 2-(2'-methylphenyl)-3-ethylquinoline-4-carbonylguanidine
118. 2-phenyl-3-n-propylquinoline-4-carbonylguanidine
119. 2-(2'-methylphenyl)-3-n-propylquinoline-4-carbonylguanidine
120. 2-phenyl-3-isopropylquinoline-4-carbonylguanidine
121. 2-(2'-methylphenyl)-3-isopropylquinoline-4-carbonylguanidine
122. 2-phenyl-3-cyclopropylquinoline-4-carbonylguanidine
123. 2-phenyl-3-n-butylquinoline-4-carbonylguanidine
124. 2-phenyl-3-tert-butylquinoline-4-carbonylguanidine
125. 2-phenyl-3-(2-methylpropyl)quinoline-4-carbonylguanidine
126. 2-phenyl-3-(1-methylpropyl)quinoline-4-carbonylguanidine
127. 2-phenyl-3-cyclobutylquinoline-4-carbonylguanidine
128. 2-phenyl-3-n-pentylquinoline-4-carbonylguanidine
129. 2-phenyl-3-(2-methylbutyl)quinoline-4-carbonylguanidine
130. 2-phenyl-3-(1-methylbutyl)quinoline-4-carbonylguanidine
131. 2-phenyl-3-(1,2-dimethylpropyl)quinoline-4-carbonylguanidine
132. 2-phenyl-3-(1,1-dimethylpropyl)quinoline-4-carbonylguanidine
133. 2-phenyl-3-(2,2-dimethylpropyl)quinoline-4-carbonylguanidine
134. 2-phenyl-3-cyclopentylquinoline-4-carbonylguanidine
135. 2-phenyl-3-n-hexylquinoline-4-carbonylguanidine
136. 2-phenyl-3-(4-methylpentyl)quinoline-4-carbonylguanidine
137. 2-phenyl-3-(3-methylpentyl)quinoline-4-carbonylguanidine
138. 2-phenyl-3-(2-methylpentyl)quinoline-4-carbonylguanidine
139. 2-phenyl-3-(1-methylpentyl)quinoline-4-carbonylguanidine
140. 2-phenyl-3-(1,2,2-trimethylpropyl)quinoline-4-carbonylguanidine
141. 2-phenyl-3-(1,1-dimethylbutyl)quinoline-4-carbonylguanidine 142. 2-phenyl-3-(1,1,2-trimethylpropyl)quinoline-4-carbonylguanidine
143. 2-phenyl-3-(2,2-dimethylbutyl)quinoline-4-carbonylguanidine
144. 2-phenyl-3-(1,3-dimethylbutyl)quinoline-4-carbonylguanidine
145. 2-phenyl-3-(2,3-dimethylbutyl)quinoline-4-carbonylguanidine
146. 2-phenyl-3-cyclohexylquinoline-4-carbonylguanidine
147. 2-phenyl-5-methylquinoline-4-carbonylguanidine
148. 2-phenyl-6-methylquinoline-4-carbonylguanidine
149. 2-phenyl-7-methylquinoline-4-carbonylguanidine
150. 2-phenyl-8-methylquinoline-4-carbonylguanidine
151. 2-(2'-methylphenyl)-5-methylquinoline-4-carbonylguanidine
152. 2-phenyl-6-ethylquinoline-4-carbonylguanidine
153. 2-phenyl-7-n-propylquinoline-4-carbonylguanidine
154. 2-phenyl-6-isopropylquinoline-4-carbonylguanidine
155. 2-phenyl-5-n-butylquinoline-4-carbonylguanidine
156. 2-phenyl-6-tert-butylquinoline-4-carbonylguanidine
157. 2-phenyl-7-(2-methylpropyl)quinoline-4-carbonylguanidine
158. 2-phenyl-8-(1-methylpropyl)quinoline-4-carbonylguanidine
159. 2-phenyl-5-cyclobutylquinoline-4-carbonylguanidine
160. 2-phenyl-6-n-pentylquinoline-4-carbonylguanidine
161. 2-phenyl-7-(2-methylbutyl)quinoline-4-carbonylguanidine
162. 2-phenyl-8-(1-methylbutyl)quinoline-4-carbonylguanidine
163. 2-phenyl-5-(1,2-dimethylpropyl)quinoline-4-carbonylguanidine
164. 2-phenyl-6-(1,1-dimethylpropyl)quinoline-4-carbonylguanidine
165. 2-phenyl-7-(2,2-dimethylpropyl)quinoline-4-carbonylguanidine
166. 2-phenyl-7-cyclopentylquinoline-4-carbonylguanidine
167. 2-phenyl-8-n-hexylquinoline-4-carbonylguanidine
168. 2-phenyl-5-(4-methylpentyl)quinoline-4-carbonylguanidine
169. 2-phenyl-6-(3-methylpentyl)quinoline-4-carbonylguanidine
170. 2-phenyl-7-(2-methylpentyl)quinoline-4-carbonylguanidine
171. 2-phenyl-8-(1-methylpentyl)quinoline-4-carbonylguanidine
172. 2-phenyl-5-(1,2,2-trimethylpropyl)quinoline-4-carbonylguanidine
173. 2-phenyl-6-(1,1-dimethylbutyl)quinoline-4-carbonylguanidine
174. 2-phenyl-7-(1,1,2-trimethylpropyl)quinoline-4-carbonylguanidine
175. 2-phenyl-8-(2,2-dimethylbutyl)quinoline-4-carbonylguanidine
176. 2-phenyl-5-(1,3-dimethylbutyl)quinoline-4-carbonylguanidine
177. 2-phenyl-6-(2,3-dimethylbutyl)quinoline-4-carbonylguanidine
178. 2-phenyl-7-cyclohexylquinoline-4-carbonylguanidine
179. 2-phenyl-5-fluoroquinoline-4-carbonylguanidine
180. 2-phenyl-5-chloroquinoline-4-carbonylguanidine
181. 2-(2'-methylphenyl)-5-fluoroquinoline-4-carbonylguanidine
182. 2-(2'-methylphenyl)-5-chloroquinoline-4-carbonylguanidine
183. 2-(2'-methylphenyl)-5-bromoquinoline-4-carbonylguanidine
184. 2-(2'-methylphenyl)-5-iodoquinoline-4-carbonylguanidine
185. 2-phenyl-6-fluoroquinoline-4-carbonylguanidine
186. 2-phenyl-6-chloroquinoline-4-carbonylguanidine
187. 2-phenyl-6-iodoquinoline-4-carbonylguanidine
188. 2-phenyl-7-bromoquinoline-4-carbonylguanidine
189. 2-phenyl-7-chloroquinoline-4-carbonylguanidine
190. 2-phenyl-8-chloroquinoline-4-carbonylguanidine
191. 2-phenyl-8-iodoquinoline-4-carbonylguanidine
192. 2-phenyl-5-nitroquinoline-4-carbonylguanidine
193. 2-phenyl-6-nitroquinoline-4-carbonylguanidine
194. 2-phenyl-7-nitroquinoline-4-carbonylguanidine
195. 2-phenyl-8-nitroquinoline-4-carbonylguanidine
196. 2-phenyl-5-aminoquinoline-4-carbonylguanidine
197. 2-phenyl-6-aminoquinoline-4-carbonylguanidine
198. 2-phenyl-7-aminoquinoline-4-carbonylguanidine
199. 2-phenyl-8-aminoquinoline-4-carbonylguanidine
200. 2-phenyl-5-hydroxyquinoline-4-carbonylguanidine
201. 2-phenyl-6-hydroxyquinoline-4-carbonylguanidine
202. 2-phenyl-7-hydroxyquinoline-4-carbonylguanidine
203. 2-phenyl-8-hydroxyquinoline-4-carbonylguanidine
204. 2-(2'-methylphenyl)-5-hydroxyquinoline-4-carbonylguanidine
205. 2-(2'-methylphenyl)-6-hydroxyquinoline-4-carbonylguanidine
206. 2-(2'-methylphenyl)-7-hydroxyquinoline-4-carbonylguanidine
207. 2-(2'-methylphenyl)-8-hydroxyquinoline-4-carbonylguanidine
208. 2-(2'-methylphenyl)-5,6-dihydroxyquinoline-4-carbonylguanidine
209. 2-(2'-methylphenyl)-5,7-dihydroxyquinoline-4-carbonylguanidine
210. 2-(2'-methylphenyl)-5,8-dihydroxyquinoline-4-carbonylguanidine
211. 2-(2'-methylphenyl)-6,7-dihydroxyquinoline-4-carbonylguanidine
212. 2-(2'-methylphenyl)-6,8-dihydroxyquinoline-4-carbonylguanidine
213. 2-(2'-methylphenyl)-7,8-dihydroxyquinoline-4-carbonylguanidine
214. 2-phenyl-5-methoxyquinoline-4-carbonylguanidine
215. 2-phenyl-6-methoxyquinoline-4-carbonylguanidine
216. 2-phenyl-7-methoxyquinoline-4-carbonylguanidine
217. 2-phenyl-8-methoxyquinoline-4-carbonylguanidine
218. 2-phenyl-5,6-dimethoxyquinoline-4-carbonylguanidine
219. 2-phenyl-5,7-dimethoxyquinoline-4-carbonylguanidine
220. 2-phenyl-5,8-dimethoxyquinoline-4-carbonylguanidine
221. 2-phenyl-6,7-dimethoxyquinoline-4-carbonylguanidine
222. 2-phenyl-6,8-dimethoxyquinoline-4-carbonylguanidine
223. 2-phenyl-7,8-dimethoxyquinoline-4-carbonylguanidine
224. 2-phenyl-5,6,7-trimethoxyquinoline-4-carbonylguanidine
225. 2-phenyl-5,6,8-trimethoxyquinoline-4-carbonylguanidine
226. 2-phenyl-5,7,8-trimethoxyquinoline-4-carbonylguanidine 227. 2-phenyl-6,7,8-trimethoxyquinoline-4-carbonylguanidine
228. 2-phenyl-5,6,7,8-tetramethoxyquinoline-4-carbonylguanidine
229. 2-(2'-methylphenyl)-5-methoxyquinoline-4-carbonylguanidine
230. 2-(2'-methylphenyl)-6-methoxyquinoline-4-carbonylguanidine
231. 2-(2'-methylphenyl)-7-methoxyquinoline-4-carbonylguanidine
232. 2-(2'-methylphenyl)-8-methoxyquinoline-4-carbonylguanidine
233. 2-(2'-methylphenyl)-5,6-dimethoxyquinoline-4-carbonylguanidine
234. 2-(2'-methylphenyl)-5,7-dimethoxyquinoline-4-carbonylguanidine
235. 2-(2'-methylphenyl)-5,8-dimethoxyquinoline-4-carbonylguanidine
236. 2-(2'-methylphenyl)-6,7-dimethoxyquinoline-4-carbonylguanidine
237. 2-(2'-methylphenyl)-6,8-dimethoxyquinoline-4-carbonylguanidine
238. 2-(2'-methylphenyl)-7,8-dimethoxyquinoline-4-carbonylguanidine
239. 2-(2'-methylphenyl)-5,6,7-trimethoxyquinoline-4-carbonylguanidine
240. 2-(2'-methylphenyl)-5,6,8-trimethoxyquinoline-4-carbonylguanidine
241. 2-(2'-methylphenyl)-5,7,8-trimethoxyquinoline-4-carbonylguanidine
242. 2-(2'-methylphenyl)-6,7,8-trimethoxyquinoline-4-carbonylguanidine
243. 2-(2'-methylphenyl)-5,6,7,8-tetramethoxyquinoline-4-carbonylguanidine
244. 2-phenyl-5-ethoxyquinoline-4-carbonylguanidine
245. 2-phenyl-6-ethoxyquinoline-4-carbonylguanidine
246. 2-phenyl-7-ethoxyquinoline-4-carbonylguanidine
247. 2-phenyl-8-ethoxyquinoline-4-carbonylguanidine
248. 2-(2'-methylphenyl)-5-ethoxyquinoline-4-carbonylguanidine
249. 2-(2'-methylphenyl)-6-ethoxyquinoline-4-carbonylguanidine
250. 2-(2'-methylphenyl)-7-ethoxyquinoline-4-carbonylguanidine
251. 2-(2'-methylphenyl)-8-ethoxyquinoline-4-carbonylguanidine
252. 2-(2'-methylphenyl)-5-n-propyloxyquinoline-4-carbonylguanidine
253. 2-(2'-methylphenyl)-6-isopropyloxyquinoline-4-carbonylguanidine
254. 2-(2'-methylphenyl)-7-cyclopropyloxyquinoline-4-carbonylguanidine
255. 2-(2'-methylphenyl)-8-n-butyloxyquinoline-4-carbonylguanidine
256. 2-(2'-methylphenyl)-5-tert-butyloxyquinoline-4-carbonylguanidine
257. 2-(2'-methylphenyl)-6-cyclobutyloxyquinoline-4-carbonylguanidine
258. 2-(2'-methylphenyl)-7-(2-methylpropyloxy)quinoline-4-carbonylguanidine
259. 2-(2'-methylphenyl)-8-(1-methylpropyloxy)quinoline-4-carbonylguanidine
260. 2-(2'-methylphenyl)-5-n-pentyloxyquinoline-4-carbonylguanidine
261. 2-(2'-methylphenyl)-6-cyclopentyloxyquinoline-4-carbonylguanidine
262. 2-(2'-methylphenyl)-7-(2-methylbutyloxy)quinoline-4-carbonylguanidine
263. 2-(2'-methylphenyl)-8-(1-methylbutyloxy)quinoline-4-carbonylguanidine
264. 2-(2'-methylphenyl)-5-(1,2-dimethylpropyloxy)quinoline-4-carbonylguanidine
265. 2-(2'-methylphenyl)-6-(1,1-dimethylpropyloxy)quinoline-4-carbonylguanidine
266. 2-(2'-methylphenyl)-7-(2,2-dimethylpropyloxy)quinoline-4-carbonylguanidine
267. 2-(2'-methylphenyl)-8-n-pentyloxyquinoline-4-carbonylguanidine
268. 2-(2'-methylphenyl)-5-cyclopentyloxyquinoline-4-carbonylguanidine
269. 2-(2'-methylphenyl)-6-(4-methylpentyloxy)quinoline-4-carbonylguanidine
270. 2-(2'-methylphenyl)-7-(3-methylpentyloxy)quinoline-4-carbonylguanidine
271. 2-(2'-methylphenyl)-8-(2-methylpentyloxy)quinoline-4-carbonylguanidine
272. 2-(2'-methylphenyl)-5-(1-methylpentyloxy)quinoline-4-carbonylguanidine
273. 2-(2'-methylphenyl)-6-(1,2,2-trimethylpropyloxy)quinoline-4-carbonylguanidine
274. 2-(2'-methylphenyl)-7-(1,1-dimethylbutyloxy)quinoline-4-carbonylguanidine
275. 2-(2'-methylphenyl)-8-(1,1,2-trimethylpropyloxy)quinoline-4-carbonylguanidine
276. 2-(2'-methylphenyl)-5-(2,2-dimethylbutyloxy)quinoline-4-carbonylguanidine
277. 2-(2'-methylphenyl)-6-(2,3-dimethylbutyloxy)quinoline-4-carbonylguanidine
278. 2-(2'-methylphenyl)-5-methoxymethyloxyquinoline-4-carbonylguanidine
279. 2-phenyl-8-methoxyethyloxyquinoline-4-carbonylguanidine
280. 2-(2'-methylphenyl)-6-ethoxymethyloxyquinoline-4-carbonylguanidine
281. 2-(2'-methylphenyl)-7-methoxymethyloxyquinoline-4-carbonylguanidine
282. 2-(2'-methylphenyl)-7-n-propyloxyethyloxyquinoline-4-carbonylguanidine
283. 2-(2'-methylphenyl)-8-isopropyloxypropyloxyquinoline-4-carbonylguanidine
284. 2-(2'-methylphenyl)-5-cyclopropyloxybutyloxyquinoline-4-carbonylguanidine
285. 2-(2'-methylphenyl)-6-n-butyloxypentyloxyquinoline-4-carbonylguanidine
286. 2-(2'-methylphenyl)-7-tert-butyloxyhexyloxyquinoline-4-carbonylguanidine
287. 2-(2'-methylphenyl)-8-(2-methylpropyloxymethyloxy)quinoline-4-carbonylguanidine
288. 2-(2'-methylphenyl)-5-(1-methylpropyloxyethyloxy)quinoline-4-carbonylguanidine
289. 2-(2'-methylphenyl)-6-n-pentyloxypropyloxyquinoline-4-carbonylguanidine
290. 2-(2'-methylphenyl)-7-cyclopentyloxymethyloxyquinoline-4-carbonylguanidine
291. 2-(2'-methylphenyl)-8-n-hexyloxypentyloxyquinoline-4-carbonylguanidine
292. 2-phenyl-5-methanesulfonylaminoquinoline-4-carbonylguanidine
293. 2-phenyl-6-methanesulfonylaminoquinoline-4-carbonylguanidine
294. 2-phenyl-7-methanesulfonylaminoquinoline-4-carbonylguanidine
295. 2-phenyl-8-methanesulfonylaminoquinoline-4-carbonylguanidine
296. 2-(2'-methylphenyl)-5-methanesulfonylaminoquinoline-4-carbonylguanidine 297. 2-(2'-methylphenyl)-6-methanesulfonylaminoquinoline-4-carbonylguanidine 298. 2-(2'-methylphenyl)-7-methanesulfonylaminoquinoline-4-carbonylguanidine 299. 2-(2'-methylphenyl)-8-methanesulfonylaminoquinoline-4-carbonylguanidine 300. 2-phenyl-5-ethanesulfonylaminoquinoline-4-carbonylguanidine 301. 2-phenyl-6-ethanesulfonylaminoquinoline-4-carbonylguanidine 302. 2-phenyl-7-n-propanesulfonylaminoquinoline-4-carbonylguanidine 303. 2-phenyl-8-isopropanesulfonylaminoquinoline-4-carbonylguanidine 304. 2-phenyl-5-n-butanesulfonylaminoquinoline-4-carbonylguanidine 305. 2-phenyl-6-tert-butanesulfonylaminoquinoline-4-carbonylguanidine 306. 2-phenyl-7-(2-methylpropanesulfonylamino)quinoline-4-carbonylguanidine 307. 2-phenyl-8-(1-methylpropanesulfonylamino)quinoline-4-carbonylguanidine 308. 2-phenyl-5-cyclobutanesulfonylaminoquinoline-4-carbonylguanidine 309. 2-phenyl-6-n-pentanesulfonylaminoquinoline-4-carbonylguanidine 310. 2-phenyl-7-cyclopentanesulfonylaminoquinoline-4-carbonylguanidine 311. 2-phenyl-8-n-hexanesulfonylaminoquinoline-4-carbonylguanidine 312. 2-phenyl-5-cyclohexanesulfonylaminoquinoline-4-carbonylguanidine 313. 2-phenyl-5-acetylaminoquinoline-4-carbonylguanidine 314. 2-phenyl-6-acetylaminoquinoline-4-carbonylguanidine 315. 2-phenyl-7-acetylaminoquinoline-4-carbonylguanidine 316. 2-phenyl-8-acetylaminoquinoline-4-carbonylguanidine 317. 2-(2'-methylphenyl)-5-acetylaminoquinoline-4-carbonylguanidine 318. 2-(2'-methylphenyl)-6-acetylaminoquinoline-4-carbonylguanidine 319. 2-(2'-methylphenyl)-7-acetylaminoquinoline-4-carbonylguanidine 320. 2-(2'-methylphenyl)-8-acetylaminoquinoline-4-carbonylguanidine 321. 2-phenyl-5-propionylaminoquinoline-4-carbonylguanidine 322. 2-phenyl-6-butyrylaminoquinoline-4-carbonylguanidine 323. 2-phenyl-7-valerylaminoquinoline-4-carbonylguanidine 324. 2-phenyl-8-hexanoylaminoquinoline-4-carbonylguanidine 325. 2-phenyl-5-isobutyrylaminoquinoline-4-carbonylguanidine 326. 2-phenyl-6-isovalerylaminoquinoline-4-carbonylguanidine 327. 2-phenyl-7-pivaloylaminoquinoline-4-carbonylguanidine 328. 2-phenyl-8-cyclopentylcarbonylaminoquinoline-4-carbonylguanidine 329. 2-(2'-methylphenyl)-5-methoxy-6-methylquinoline-4-carbonylguanidine 330. 2-(2'-methylphenyl)-5-methoxy-7-methylquinoline-4-carbonylguanidine 331. 2-(2'-methylphenyl)-5-methoxy-8-methylquinoline-4-carbonylguanidine 332. 2-(2'-methylphenyl)-5-methyl-8-methoxyquinoline-4-carbonylguanidine 333. 2-(2'-methylphenyl)-6-methyl-8-methoxyquinoline-4-carbonylguanidine 334. 2-(2'-methylphenyl)-7-methyl-8-methoxyquinoline-4-carbonylguanidine 335. 2-(2'-methylphenyl)-5-methoxy-6-fluoroquinoline-4-carbonylguanidine 336. 2-(2'-methylphenyl)-5-methoxy-7-chloroquinoline-4-carbonylguanidine 337. 2-(2'-methylphenyl)-5-methoxy-8-bromoquinoline-4-carbonylguanidine 338. 2-(2'-methylphenyl)-5-methoxy-8-iodoquinoline-4-carbonylguanidine 339. 2-(2'-methylphenyl)-5-fluoro-8-methoxyquinoline-4-carbonylguanidine 340. 2-(2'-methylphenyl)-5-chloro-8-methoxyquinoline-4-carbonylguanidine 341. 2-(2'-methylphenyl)-5-iodo-8-methoxyquinoline-4-carbonylguanidine 342. 2-(2'-methylphenyl)-5-bromo-8-methoxyquinoline-4-carbonylguanidine 343. 2-phenyl-6-chloro-8-methylquinoline-4-carbonylguanidine 344. 2-phenyl-5-methoxy-8-methanesulfonylaminoquinoline-4-carbonylguanidine 345. 2-phenyl-5-methanesulfonylamino-8-methoxyquinoline-4-carbonylguanidine 346. 2-(2'-methylphenyl)-5-methoxy-8-methanesulfonylaminoquinoline-4-carbonylguanidine 347. 2-(2'-methylphenyl)-5-methanesulfonylamino-8-methoxyquinoline-4-carbonylguanidine 348. 2-phenyl-3-methyl-5,7-dimethoxyquinoline-4-carbonylguanidine 349. 2-phenyl-3-methyl-5,8-dimethoxyquinoline-4-carbonylguanidine 350. 2-(2'-methylphenyl)-3-methyl-5,7-dimethoxyquinoline-4-carbonylguanidine 351. 2-(2'-methylphenyl)-3-methyl-5,8-dimethoxyquinoline-4-carbonylguanidine When the compounds of formula (1) and pharmaceutically acceptable salts thereof in the present invention are used as an agent for treating or preventing hypertension, arrhythmia, diseases owing to ischemia which is a primary or secondary cause and diseases caused by cell growth and organic hyperplasia or hypertrophy (all of these result from activation of NHE), the above-mentioned compounds and salts can be administered either orally or parenterally. The form thereof varies with the properties of the compounds of the present invention which are used as an active ingredient.

The preparations of these compounds can be obtained by a known method. These preparations can take various forms depending on therapeutic purposes. Typical forms are solids, solutions, suppositories and the like. More specifically, the solids are tablets, pills, powders, granules and capsules. The solutions are injections, suspensions, syrups and emulsions.

When tablets are prepared, it is possible to use various carriers which have been well known in this field so far. Examples of the carriers include excipients such as lactose, sucrose, sodium chloride, glucose, urea, starch, calcium carbonate, kaolin, crystalline cellulose, and silicic acid; binders such as water, ethanol, propanol, simple syrup, liquid glucose, starch solution, gelatin solution, shellac solution, methyl cellulose solution, hydroxypropyl cellulose solution, polyvinyl pyrrolidone solution, and carboxymethyl cellulose solution; disintegrants such as dry starch, sodium alginate, agar powder, sodium hydrogencarbonate, calcium carbonate, polyoxyethylenesorbitan fatty acid esters, sodium laurylsulfate, stearic acid glyceride, starch, and lactose; disintegration suppressants such as sucrose, stearic acid, cocoa butter, and hydrogenated oil; absorption accelerators such as quaternary ammonium base, and sodium laurylsulfate; wetting agents such as glycerin, and starch; adsorbents such as starch, lactose, kaolin, bentonite, colloidal silicic acid, crystalline cellulose, and light silicic anhydride; and lubricants such as talc, stearate salt, boric acid powder, and polyethylene glycol.

Further, in the case of tablets, coated tablets can be formed as required. Examples of the coated tablets include sugar-coated tablets, gelatin-coated tablets, enteric coated tablets, and film-coated tablets. Two-layered tablets and multi-layered tablets are also available.

In the case of pills, a carrier which is known in this field can be used. Examples of the carrier include excipients such as glucose, lactose, starch, cocoa butter, hydrogenated vegetable oil, kaolin, and talc; binders such as gum arabic, tragacanth powder, and gelatin; and disintegrants such as carmellose calcium, and agar.

In the case of capsules, usually, the active ingredient compound is mixed with the above-mentioned carrier, and the mixture is filled in a hard gelatin capsule, a soft capsule or the like.

In the case of injections, a known diluent is used in forming a solution, an emulsion or a suspension. Examples of the diluent include water, ethanol, macrogel, propylene glycol, ethoxyisostearyl alcohol, polyoxyisostearyl alcohol, polyoxyethylenesorbitan fatty acid esters, cottonseed oil, corn oil, peanut oil, olive oil and the like. Further, a suspension is prepared in the presence of an appropriate surfactant by adding water to the compound of the present invention, or an emulsion is formed using a surfactant such as polyoxyethylene-hardened castor oil (HCO-60), Polysorbate 80 or polyethylene glycol. Sodium chloride, glucose or glycerin may be contained in pharmaceutical preparations, or an ordinary dissolution aid, buffer or analgesic may be added thereto.

In the case of suppositories, a known carrier can be used. Examples of the carrier include polyethylene glycol, cocoa butter, higher alcohol, higher alcohol esters, gelatin, and semi-synthetic glyceride.

Besides, a colorant, a preservative, a flavor, a seasoning, a sweetener and the like can be contained in pharmaceutical preparations.

A method of administering the pharmaceutical preparations of the present invention is not particularly limited, and it depends on the age, sex and other conditions of patients, and stages of diseases. For example, tablets, pills, solutions, suspensions, emulsions, powders, granules, syrups and capsules are administered orally. Injections are administered intravenously either singly or in combination with an ordinary aid such as glucose, amino acids or the like. Further, injections are administered intramuscularly, subcutaneously or intraperitoneally as required. Suppositories are administered intrarectally.

The dose of these pharmaceutical preparations in the present invention is approximately selected depending on usage, the age, sex and other conditions of patients, and stages of diseases. The dose of the active ingredient compound for adults is preferably between approximately 0.001 and 1,000 mg. The amount of the active ingredient compound in the preparation in administration unit form is preferably between approximately 0.001 and 1,000 mg.

The present invention will be illustrated specifically by referring to the following Production Reference Examples, Examples, Preparation Examples and Test Examples. However, the present invention is not limited thereto.

EXAMPLES

Reference Example 1

Synthesis of 2-(4'-methylphenyl)quinoline-4-carboxylic Acid

Ten milliliters (2.2N) of a sodium hydroxide aqueous solution was added dropwise to an ethanol (20 ml) suspension containing 1.47 g of isatin and 2.67 ml of 4-methylacetophenone at room temperature, and the reaction mixture was then heat-refluxed for 5.5 hours. The resulting reaction mixture was allowed to cool, and then acidified with 2N sulfuric acid to obtain an orange-colored precipitate. This precipitate was collected by filtration, and dried to form 2.34 g of the above-mentioned compound.

$^1$H-NMR(DHSO-d$^-$$_6$), δ: 2.55(s, 3H), 7.32–7.40(m, 3H), 7.66–7.71(m, 1H), 7.86(d, 1H), 8.15(d, 1H), 8.21(d, 1H), 8.43(s, 1H), 8.64(d, 2H)

Reference Example 2

Synthesis of 2-(3'-methylphenyl)quinoline-4-carboxylic Acid

The above-mentioned compound (0.62 g) was formed from 1.47 g of isatin and 2.68 g of 3-methylacetophenone in the same manner as in Reference Example 1.

$^1$H-NMR(DMSO-d$_6$), δ: 2.46(s, 3H), 7.34(d, 1H), 7.47(t. 1H), 7.70(t, 1H), 7.86(t, 1H), 8.13(m, 3H), 8.46(s, 1H), 8.66(d, 1H)

Reference Example 3

Synthesis of 2- (2'-methylphenyl)quinoline-4-carboxylic Acid

The above-mentioned compound (0.89 g) was formed from 1.47 g of isatin and 2.68 g of 2-methylacetophenone in the same manner as in Reference Example 1.

$^1$H-NMR(DMSO-d$_6$), δ: 2.42(s, 3H), 7.39(m, 3H), 7.55 (m, 1H), 7.74(t, 1H), 7.87(t, 1H), 8.05(s, 1H), 8.14(d, 1H), 8.74(d, 1H)

Reference Example 4

Synthesis of 2-(2',4'-dimethylphenyl)quinoline-4-carboxylic Acid

The above-mentioned compound (1.00 g) was formed from 1.47 g of isatin and 2.96 g of 2,4-dimethylacetophenone in the same manner as in Reference Example 1.

$^1$H-NMR(DNSO-d$_6$), δ: 2.37(s, 3H), 2.40(s, 3H), 7.17(d, 2H), 7.40(d, 1H), 7.72(t, 1H), 7.85(t, 1H), 8.02(s, 1H). 8.12(d, 1H), 8.72(d, 1H)

Reference Example 5

Synthesis of 2-(3',4'-dimethylphenyl)quinoline-4-carboxylic Acid

The above-mentioned compound (4.35 g) was formed from 2.0 g of isatin and 4.0 g of 3,4-dimethylacetophenone in the same manner as in Reference Example 1.

¹H-NMR(DMSO-d₆), δ: 2.32(s, 3H), 2.37(s, 3H),7.33(d, 1H), 7.64–7.68(m, 1H), 7.70–7.86(m, 1H), 8.00–8.17(m, 3H), 8.43(s, 1H), 8.65(d, 1H)

Reference Example 6

Synthesis of 2-(2',4',6'-trimethylphenyl)quinoline-4-carboxylic Acid

The above-mentioned compound (0.16 g) was formed from 2.21 g of isatin and 4.87 g of 2,4,6-trimethylacetophenone in the same manner as in Reference Example 1.

¹H-NMR(DMSO-d₆), δ: 1.98(s, 6H), 2.32(s, 3H), 6.99(s, 2H), 7.75(t, 1H), 7.78(s, 1H), 7.86(t, 1H), 8.11(d, 1H), 8.75(d, 1H) m.p. 240° C. (decomp.)

Reference Example 7

Synthesis of 2-(4'-tert-butylphenyl)quinoline-4-carboxylic Acid

The above-mentioned compound (0.70 g) was formed from 1.47 g of isatin and 3.60 g of 4-tert-butylacetophenone in the same manner as in Reference Example 1.

¹H-NMR(DMSO-d₆), δ: 1.37(s, 9H), 7.55(m, 3H), 7.76(t, 1H), 8.12(d, 2H), 8.27(d, 1H), 8.46(s, 1H), 8.82(d, 1H)

Reference Example 8

Synthesis of 2-(3'-trifluoromethylphenyl)quinoline-4-carboxylic Acid

The above-mentioned compound (1.89 g) was formed from 1.47 g of isatin and 3.76 g of 3-trifluoromethylacetophenone in the same manner as in Reference Example 1.

¹H-NMR(DMSO-d₆), δ: 7.75–7.92(m, 4H), 8.24(d, 1H), 8.60(s, 1H), 8.65(m, 3H)

Reference Example 9

Synthesis of 2-(2'-trifluoromethylphenyl)quinoline-4-carboxylic Acid

The above-mentioned compound (2.85 g) was formed from 1.90 g of isatin and 5.0 g of 2-trifluoromethylacetophenone the same manner as in Reference Example 1.

¹H-NMR(DMSO-d₆), δ: 7.76(m, 2H), 7.78(s, 1H), 7.79(s, 1H), 7.90(m, 2H), 8.03(s, 1H), 8.14(d, 1H)

Reference Example 10

Synthesis of 2-(4'-bromophenyl)quinoline-4-carboxylic Acid

The above-mentioned compound (3.00 g) was formed from 1.47 g of isatin and 3.98 g of 4-bromoacetophenone in the same manner as in Reference Example 1.

¹H-NMR(DMSO-d₆), δ: 7.73–7.84(m, 4H), 8.17(d, 1H), 8.28(d, 2H), 8.47(s, 1H), 8.65(d, 1H)

Reference Example 11

Synthesis of 2-(4'-fluorophenyl)quinoline-4-carboxylic Acid

The above-mentioned compound (2.21 g) was formed from 1.47 g of isatin and 2.76 g of 4-fluoroacetophenone in the same manner as in Reference Example 1.

¹H-NMR(DMSO-d₆), δ: 7.31–7.44(m, 2H), 7.68–7.74(m, 1H), 7.83–7.93(m, 1H), 8.16(d, 1H), 8.35–8.40(m, 2H), 8.47(s, 1H), 8.64(d, 1H)

Reference Example 12

Synthesis of 2-(2'-chlorophenyl)quinoline-4-carboxylic Acid

The above-mentioned compound (0.90 g) was formed from 1.47 g of isatin and 3.1 g of 2-chloroacetophenone in the same manner as in Reference Example 1.

¹H-NMR(DMSO-d₆), δ: 7.12(t, 1H), 7.21(d, 1H), 7.48(t, 1H), 7.81(t, 1H), 7.78(m, 2H), 7.99(d, 1H), 8.08(s, 1H), 8.74(d, 1H)

Reference Example 13

Synthesis of 2-(4'-methoxyphenyl)quinoline-4-carboxylic Acid

The above-mentioned compound (1.54 g) was formed from 1.47 g of isatin and 3.0 g of 4-methoxyacetophenone in the same manner as in Reference Example 1.

¹H-NMR(DMSO-d₆), δ: 3.86(s, 3H), 7.13(d, 2H), 7.62–7.68(m, 1H), 7.79–7.85(m, 1H), 7.94(d, 1H), 8.27(d, 2H), 8.39(s, 1H), 8.61(d, 1H)

Reference Example 14

Synthesis of 2-(2'-methoxyphenyl)quinoline-4-carboxylic Acid

The above-mentioned compound (0.91 g) was formed from 1.47 g of isatin and 3.0 g of 2-methoxyacetophenone in the same manner as in Reference Example 1.

¹H-NMR(DMSO-d₆), δ:3.89(s, 3H), 7.14(t, 1H), 7.22(d, 1H), 7.50(t, 1H), 7.72(t, 1H), 7.85(m, 2H), 8.13(d, 1H), 8.33(s, 1H), 8.92(d, 1H)

Reference Example 15

Synthesis of 2-(2',6'-dimethoxyphenyl)quinoline-4-carboxylic Acid

The above-mentioned compound (0.59 g) was formed from 1.50 g of isatin and 3.68 g of 2,6-dimethoxyacetophenone in the same manner as in Reference Example 1.

¹H-NMR(DMSO-d₆), δ: 3.64(s, 6H), 6.76(s, 1H), 6.80(s, 1H), 7.40(t, 1H), 7.46(s, 1H), 7.55(t, 1H), 7.69(t, 1H), 7.95(d, 1H), 8.75(d, 1H)

Reference Example 16

Synthesis of 2-(4'-trifluoromethoxyphenyl)quinoline-4-carboxylic Acid

The above-mentioned compound (2.27 g) was formed from 1.47 g of isatin and 4.08 g of 4-trifluoromethoxyacetophenone in the same manner as in Reference Example 1.

¹H-NMR(DMSO-d₆), δ: 7.55(d, 2H), 7.72(t, 1H), 7.87(t, 1H), 8.19(d, 1H), 8.41(d, 2H), 8.49(s, 1H), 8.68(d, 1H)

Reference Example 17

Synthesis of 2-phenyl-3-methylquinoline-4-carboxylic Acid

Ten milliliters (2N) of a sodium hydroxide aqueous solution was added dropwise to an ethanol (20 ml) suspension containing 1.47 g of isatin and 2.68 g of propiophenone at room temperature, and the reaction mixture was then heat-refluxed for 26 hours. The resulting reaction mixture was allowed to cool, and then concentrated under reduced pressure. Ice water was added to the residue, and the mixture was extracted with ethyl ether. The aqueous layer was acidified with dilute hydrochloric acid. The precipitate was collected by filtration, and dried to form 1.47 g of the above-mentioned compound.

$^1$H-NMR(DMSO-d$_6$), δ: 2.39(s, 3H), 7.53–7.70(m, 6H), 7.71–7.83(m, 2H), 8.05(d, 1 g)

Reference Example 18

Synthesis of 2-phenyl-6-fluoroquinoline-4-carboxylic Acid

The above-mentioned compound (1.58 g) was formed from 1.65 g of 5-fluoroisatin and 2.40 g of acetophenone in the same manner as in Reference Example 1.

$^1$H-NMR(DMSO-d$_6$), δ: 7.55(m, 3H), 7.80(m, 1H), 8.26 (m, 1H), 8.48(m, 1H), 8.50(m, 1H), 8.56(s, 1H)

Reference Example 19

Synthesis of 2-phenyl-6-iodoquinoline-4-carboxylic Acid

The above-mentioned compound (2.01 g) was formed from 2.73 g of 5-iodoisatin and 2.40 g of acetophenone in the same manner as in Reference Example 1.

$^1$H-NMR(DMSO-d$_6$), δ:7.57(m, 3H), 7.92(d, 1H), 8.12 (m, 1H), 8.28(m, 2H), 8.51(s, 1H), 9.15(s, 1H)

Reference Example 20

Synthesis of 2-phenyl-5-chloroquinoline-4-carboxylic Acid

The above-mentioned compound (0.42 g) was formed from 0.70 g of 4-chloroisatin prepared by a known method [A. E. Senear, J. Am. Chem. Soc., 68, 2695–2697 (1946)] and 0.82 ml of acetophenone in the same manner as in Reference Example 1.

$^1$H-NMR(DMSO-d$_6$), δ: 7.52–7.62(m, 3H), 7.81–7.86(m, 2H), 8.16(dd, 1H), 8.26(s, 1H), 8.33–8.37(m, 2H)

Reference Example 21

Synthesis of 2-phenyl-6-chloroquinoline-4-carboxylic Acid

The above-mentioned compound (1.72 g) was formed from 1.47 g of 5-chloroisatin and 3.10 g of acetophenone in the same manner as in Reference Example 1.

$^1$H-NNR(DMSO-d$_6$), δ: 7.61(s, 1H), 7.64(s, 1H), 7.71(t, 1H), 7.86(t, 1H), 8.16(t, 1H), 8.35(s, 1H), 8.36(s, 1H), 8.47(s, 1H),8.67(d, 1H)

Reference Example 22

Synthesis of 2-phenyl-7-chloroquinoline-4-carboxylic Acid

The above-mentioned compound (1.26 g) was formed from 1.0 g of 6-chloroisatin prepared by a known method (A. E. Senear, J. Am. Chem. Soc., 68, 2695–2697 (1946)] and 1.3 ml of acetophenone in the same manner as in Reference Example 1.

$^1$H-NMR(DNSO-d$_6$), δ: 7.53–7.64(m, 3H), 7.74(dd, 1H), 8.21–8.30(m, 3H), 8.49(s, 1H), 8.73(d, 1H)

Reference Example 23

Synthesis of 2-phenyl-6-chloro-8-methylquinoline-4-carboxylic Acid

The above-mentioned compound (1.03 g) was formed from 1.95 g of 5-chloro-7-methylisatin and 2.40 g of acetophenone in the same manner as in Reference Example 1.

$^1$H-NMR(DMSO-d$_6$), δ: 2.53(s,3H), 7.55(m,3H), 7.65(d, 1H), 8.03(d, 1H), 8.25(d, 2H), 8.35(s, 1H), 8.46(s, 1H)

Reference Example 24

Synthesis of 2-phenyl-6-methylquinoline-4-carboxylic Acid

Benzaldehyde (2.12 g) and 2.14 g of p-toluidine were dissolved in 50 ml of ethanol, and 1.76 g of pyruvic acid were added thereto dropwise. The reaction mixture was then heat-refluxed for 6 hours. The resulting reaction mixture was cooled to room temperature, and then concentrated under reduced pressure. The residue was dissolved in a 1N sodium hydroxide aqueous solution. This aqueous solution was extracted with ethyl ether, and the aqueous layer was acidified with dilute hydrochloric acid. The precipitate was collected by filtration, and dried to form 0.51 g of the above-mentioned compound.

$^1$H-NMR(DMSO-d$_6$), δ: 2.54(s.3H), 7.54(a, 3H), 7.69(d, 1H), 8.05(d, 1H), 8.26(d, 2H), 8.37(s, 1H), 8.44(s, 1H)

Reference Example 25

Synthesis of 2-(3'-nitrophenyl)quinoline-4-carboxylic Acid

The above-mentioned compound (0.75 g) was formed from 6.86 g of 3-nitrobenzaldehyde, 4.9 g of aniline and 2.0 g of pyruvic acid in the same manner as in Reference Example 24.

$^1$H-NMR(DMSO-d$_6$), δ: 7.25–7.36(m, 1H), 7.85–7.91(m, 2H), 8.20–8.31(m, 1H), 8.37–8.40(m, 1H), 8.60(s, 1H), 8.69(d, 1H), 8.76(d, 1H), 9.10–9.12(m, 1H)

Reference Example 26

Synthesis of 2-(2'-isopropylphenyl)quinoline-4-carboxylic Acid

The above-mentioned compound (1.48 g) was formed from 1.4 g of 2-isopropylbenzaldehyde prepared by a known method [Chem. Pharm. Bull., 35, 1953–1968 (1987)], 0.88 g of aniline and 0.83 g of pyruvic acid in the same manner as in Reference Example 24.

$^1$H-NMR(DMSO-d$_6$), δ: 1.18(d,6H), 3.16–3.21(m, 1H), 7.32–7.53(m,4H), 7.71(t, 1H), 7.84(t, 1H), 7.92(s, 1H), 8.10(d, 1H), 8.73(d, 1H)

Reference Example 27

Synthesis of 2-phenyl-7-methylquinoline-4-carboxylic Acid

The above-mentioned compound (1.30 g) was formed from 4.0 g of benzaldehyde, 4.0 g of m-toluidine and 3.28 g of pyruvic acid in the same manner as in Reference Example 24.

$^1$H-NMR(DMSO-d$_6$), δ: 2.56(s,3H), 7.52–7.61(m, 4H), 7.97(s, 1H), 8.25(d, 1H), 8.36(s, 1H), 8.56(d, 1H)

m.p. 233°–237° C.

Reference Example 28

Synthesis of 2-phenyl-8-methylquinoline-4-carboxylic Acid

The above-mentioned compound (1.74 g) was formed from 3.96 g of benzaldehyde, 4.0 g of o-toluidine and 3.28 g of pyruvic acid in the same manner as in Reference Example 24.

$^1$H-NMR(DMSO-d$_6$), δ: 2.85(s, 3H), 7.50–7.62(m, 4H), 7.71(d, 1H), 8.33–8.36(m,2H), 8.47 (d, 2H)

Reference Example 29

Synthesis of 2-phenyl-6-isopropylquinoline-4-carboxylic Acid

The above-mentioned compound (1.23 g) was formed from 1.59 g of benzaldehyde, 1.35 g of 4-isopropylaniline and 1.32 g of pyruvic acid in the same manner as in Reference Example 24.

$^1$H-NMR(DNSO-d$_6$), δ: 1.26(d,6H), 2.96–3.03(m, 1H), 7.36–7.65(m, 4H), 8.10–8.18(m, 3H), 8.44(s, 1H), 8.64(s, 1H)

Reference Example 30

Synthesis of 2-phenyl-8-chloroquinoline-4-carboxylic Acid

The above-mentioned compound (0.48 g) was formed from 2.12 g of benzaldehyde, 2.60 g of 2-chloroaniline and 1.80 g of pyruvic acid in the same manner as in Reference Example 24.

$^1$H-NMR(DMSO-d$_6$), δ: 7.47–7.78(m, 4H), 8.06(d, 1H), 8.32(d,2H), 8.57(s, 1H), 8.64(d, 1H)

Reference Example 31

Synthesis of 2-phenyl-6-methoxyquinoline-4-carboxylic Acid

The above-mentioned compound (0.63 g) was formed from 3.3 g of benzaldehyde, 3.83 g of p-anisidine and 2.37 g of pyruvic acid in the same manner as in Reference Example 24.

$^1$H-NMR(DMSO-d$_6$), δ: 3.93(s, 3H), 7.50–7.60(m, 4H), 8.08–8.15(m, 2H), 8.24(d, 2H), 8.46(s, 1H)

Reference Example 32

Synthesis of 2-phenyl-7-methoxyquinoline-4-carboxylic Acid

The above-mentioned compound (2.82 g) was formed from 5.31 g of benzaldehyde, 6.16 g of m-anisidine and 4.40 g of pyruvic acid in the same manner as in Reference Example 24.

$^1$H-NMR(DMSO-d$_6$), δ: 3.98(s, 3H), 7.37(d, 1H), 7.58(m, 4H), 8.27(m, 3H), 8.57(d, 1H)

Reference Example 33

Synthesis of 2-phenyl-8-methoxyquinoline-4-carboxylic Acid

The above-mentioned compound (2.45 g) was formed from 3.47 g of benzaldehyde, 4.03 g of o-anisidine and 2.90 g of pyruvic acid in the same manner as in Reference Example 24.

$^1$H-NMR(DHSO-d$_6$), δ: 4.04(s, 3H), 7.30(d, 1H), 7.53–7.66(m, 4H), 8.14(d, 1H), 8.28(d, 2H), 8.44 (s, 1H)

Reference Example 34

Synthesis of 2-phenyl-5,7-dimethoxyquinoline-4-carboxylic Acid

The above-mentioned compound (0.93 g) was formed from 1.06 g of benzaldehyde, 1.68 g of 3,5-dimethoxyaniline and 0.90 g of pyruvic acid in the same manner as in Reference Example 24.

$^1$H-NMR(dMSO-d$_6$), δ: 3.91(s, 3H), 3.95(s, 3H), 6.73(s, 1H), 7.12(s, 1H), 7.54(m, 3H), 7.83(s, 1H), 8.29(m, 2H) m.p. 240°–240.5° C. (decomp.)

Reference Example 35

Synthesis of 2-(2'-methylphenyl)-5,7-dimethoxyquinoline-4-carboxylic Acid

The above-mentioned compound (0.86 g) was formed from 3.60 g of o-tolualdehyde, 4.60 g of 3,5-dimethoxyaniline and 2.64 g of pyruvic acid in the same manner as in Reference Example 24.

$^1$H-NMR(DMSO-d$_6$), δ: 2.35(s, 3H), 3.83(s, 3H),3.89(s, 3H), 6.58(s, 1H), 6.95(s, 1H), 7.01(s, 1H), 7.30(m, 3H), 7.40(d, 1H)

Reference Example 36

Synthesis of 2-phenyl-6,7-dimethoxyquinoline-4-carboxylic Acid

The above-mentioned compound (1.58 g) was formed from 3.18 g of o-benzaldehyde, 4.60 g of 3,4-dimethoxyaniline and 2.64 g of pyruvic acid in the same manner as in Reference Example 24.

$^1$H-NNR(DMSO-d$_6$), δ: 3.96(s, 3H), 4.01(s, 3H), 7.53(m, 4H), 8.15(s, 1H), 8.20(s, 1H), 8.25(s, 1H), 8.33(s, 1H)

Reference Example 37

Synthesis of 2-(2'-methylphenyl )-6,7-dimethoxyquinoline-4-carboxylic Acid

The above-mentioned compound (3.15 g) was formed from 2.40 g of o-tolualdehyde, 3.00 g of 3,4-dimethoxyaniline and 1.70 g pyruvic acid in the same manner as in Reference Example 24.

$^1$H-NMR(DMSO-d$_6$), δ: 2.39(s, 3H), 3.95(s, 3H), 3.9.7(s, 3H), 7.17–7.20(m, 1H), 7.33–7.38(m, 2H), 7.48–7.51(m, 2H), 7.88(s, 1H), 8.20(s, 1H)

Reference Example 38

Synthesis of 2-phenyl-6,8-dimethoxyquinoline-4-carboxylic Acid

The above-mentioned compound (0.89 g) was formed from 2.12 g of benzaldehyde, 3.06 g of 2,4-dimethoxyaniline and 1.76 g of pyruvic acid in the same manner as in Reference Example 24.

$^1$H-NMR(DMSO-d$_6$), δ: 3.85(s,3H), 3.98(s, 3H), 6.82(s, 1H), 7.48(m, 3H), 7.83(s, 1H), 8.19(d, 2H), 8.30(s, 1H)

Reference Example 39

Synthesis of 2-(2'-methylphenyl)-6,8-dimethoxyquinoline-4-carboxylic Acid

The above-mentioned compound (1.69 g) was formed from 2.40 g of o-tolualdehyde, 3.06 g of 2,4-dimethoxyaniline and 1.76 g of pyruvic acid in the same manner as in Reference Example 24.

$^1$H-NMR(DMSO-$d_6$), δ: 2.39(s, 3H), 3.92(s, 3H), 3.97(s, 3H), 6.93(d, 1H), 7.36(m, 3H), 7.49(m, 1H), 7.73(d, 1H), 8.03(s, 1H)

Reference Example 40

Synthesis of 2-(2'-methylphenyl)-5,8-dimethoxyquinoline-4-carboxylic Acid

The above-mentioned compound (3.44 g) was formed from 3.60 g of o-tolualdehyde, 4.60 g of 2,5-dimethoxyaniline and 2.64 g of pyruvic acid in the same manner as in Reference Example 24.

$^1$H-NMR(DMSO-$d_6$), δ: 2.34(s, 3H), 3.79(s, 3H), 3.89(s, 3H), 6.86(d, 1H), 7.06(d, 1H), 7.25(s, 1H), 7.31(m, 4H)

m.p. 234°–235° C. (decomp.)

Reference Example 41

Synthesis of 2-(2'-methylphenyl)-7,8-dimethoxyquinoline-4-carboxylic Acid

The above-mentioned compound (2.25 g) was formed from 2.30 g of o-tolualdehyde, 2.90 g of 2,3-dimethoxyaniline and 1.66 g of pyruvic acid in the same manner as in Reference Example 24.

$^1$H-NMR(DMSO-$d_6$), δ: 2.44(s, 3H), 3.95(s, 3H), 4.00(s, 3H), 7.13–7.16(m, 1H), 7.33–7.45(m, 2H), 7.54–7.57(m, 1H), 7.66(d, 1H), 7.88(s, 1H), 8.46(d, 1H)

Reference Example 42

Synthesis of 2-phenyl-8-methoxyethyloxyquinoline-4-carboxylic Acid

The above-mentioned compound (1.40 g) was formed from 1.14 g of benzaldehyde, 1.80 g of 2-methoxyethytoxyaniline and 0.95 g of pyruvic acid in the same manner as in Reference Example 24.

$^1$H-NMR(DMSO-$d_6$), δ: 3.52(s, 3H), 3.87(t, 2H), 4.38(t, 2H),7.30(d, 1H), 7.49–7.60(m, 4H), 8:17(d, 1H), 8.29(d, 2H), 8.42(s, 1H)

m.p. 128°–133° C.

Reference Example 43

Synthesis of 2-(2'-methylphenyl)-7-methoxymethyloxyquinoline-4-carboxylic Acid

The above-mentioned compound (1.26 g) was formed from 2.74 g of o-tolualdehyde, 3.50 g of 3-methoxymethyloxyanitine and 2.00 g of pyruvic acid in the same manner as in Reference Example 24.

$^1$H-NMR(DMSO-$d_6$), δ: 2.40(s, 3H), 3.41(s, 3H), 5.41(s, 2H), 7.34–7.63(m, 6H), 7.88(s, 1H), 8.68(d, 1H)

Reference Example 44

Synthesis of ethyl 2-phenyl-8-nitroquinoline-4-carboxylate

Benzaldehyde (19.5 g), 25.6 g of 2-nitroaniline and 16.2 g of pyruvic acid were mixed, and 10.4 ml of conc. sulfuric acid were added thereto dropwise at room temperature. After the mixture was stirred for 30 minutes, chloroform, water and aqueous ammonia were added to the reaction mixture, and the aqueous layer was extracted. This aqueous layer was acidified with conc. hydrochloric acid to obtain 25.0 g of crude 2-phenyl-8-nitroquinone-4-carboxylic acid as a dark red semi-solid. This semi-solid was dissolved in 300 ml of ethanol, and 37 ml of conc. sulfuric acid were added thereto. The mixture was heat-refluxed for 6 hours. After the reaction mixture was cooled to room temperature, the precipitate formed was collected by filtration, and recrystallized from methyl ethyl ketone to form 2.50 g of the above-mentioned compound.

$^1$H-NMR(DMSO-$d_6$), δ: 1.46(t, 3H), 4.51(q, 2H), 7.56–7.65(m, 3H), 7.83–7.89(t, 1H), 8.23–8.28(m, 2H), 8.35 (d, 1H), 8.64(s, 1H), 8.81(d, 1H)

m.p. 138°–140° C.

Reference Example 45

Synthesis of 2-phenyl-8-nitroquinone-4-carboxylic Acid

Ethyl 2-phenyl-8-nitroquinone-4-carboxylic acid (1.09 g) formed in Reference Example 44 was suspended in 8 ml of ethanol, and 1.2M (6 ml) of a sodium hydroxide aqueous solution was added thereto at room temperature. The mixture was then stirred at approximately 40° C. for 2 hours. The reaction mixture was cooled with ice, and neutralized with dilute hydrochloric acid. The crystals precipitated were collected by filtration, washed with water, and dried to obtain 0.97 g of the above-mentioned compound.

$^1$H-NMR(DMSO-$d_6$), δ: 7.60(m, 3H), 7.86(t, 1H), 8.28 (m, 2H), 8.38(d, 1H), 8.66(s, 1H), 8.91(d, 1H)

Reference Example 46

Synthesis of ethyl 2-phenyl-8-aminoquinoline-4-carboxylate

Ethyl 2-phenyl-8-nitroquinone-4-carboxylate (2.0 g) formed in Reference Example 44 was hydrogenated in DMF in the presence of Pd/C in a usual manner to obtain 1.70 g of the above-mentioned compound.

$^1$H-NNR(DMSO-$d_6$), δ: 1.43(t, 3H), 4.50(q, 2H), 6.96(d, 1H), 7.36(t, 1H), 7.51–7.62(m, 4H), 8.27–8.37(m 3H)

m.p. 66°–69° C.

Reference Example 47

Synthesis of ethyl 2-phenyl-8-acetylaminoquinoline-4-carboxylate

Ethyl 2-phenyl-8-aminoquinoline-4-carboxylate (0.82 g) formed in Reference Example 46 was acetylated in a usual manner to obtain 0.75 g of the above-mentioned compound.

$^1$H-NMR(DMSO-$d_6$), δ: 1.44(t, 3H), 2.35(s, 3H), 4.50(q, 2H), 7.63(m, 4H), 8.12(d, 1H), 8.44(m, 2H), 8.52(s, H), 8.66(d, 1H), 10.12(s, H)

m.p. 141.5°–142° C.

Reference Example 48

Synthesis of 2-phenyl-8-acetylaminoquinoline-4-carboxylic Acid

Ethyl 2-phenyl-8-acetylaminoquinoline-4-carboxylate (0.67 g) formed in Reference Example 47 was suspended in 6 ml of methanol, and 4 ml (1.1M) of a sodium hydroxide aqueous solution were added thereto at room temperature. The mixture was then stirred at approximately 40° C. for 1 hour. The reaction mixture was cooled with ice, and neutralized with dilute hydrochloric acid. The precipitate was collected by filtration, and dried to obtain 0.46 g of the above-mentioned compound.

$^1$H-NMR(DMSO-$d_6$), δ: 2.35(s, 3H), 7.54–7.68(m, 4H), 8.27(d, 1H), 8.39(dd, 2H), 8.52(s, 1H), 8.65(d, 1H), 10.13(s, 1H)

m.p. 254°–255° C. (decomp.)

Reference Example 49

Synthesis of ethyl 2-phenyl-8-methanesulfonylaminoquinoline-4-carboxylate

Ethyl 2-phenyl-8-aminoquinoline-4-carboxylate (1.02 g) formed in Reference Example 46 was methanesulfonylated in a usual manner to obtain 1.16 g of the above-mentioned compound.

$^1$H-NMR(DMSO-$d_6$), δ: 1.44(t, 3H), 3.17(s, 3H), 4.51(q, 2H), 7.63(m, 4H), 7.72(t, 1H), 7.83(d, 1H), 8.44(s, 1H), 8.46(s, 1H), 8.54(s, 1H), 9.63(s, 1H)

m.p. 145.5°–146.2° C.

Reference Example 50

Synthesis of 2-phenyl-8-methanesulfonylaminoquinoline-4-carboxylate

Ethyl 2-phenyl-8-methanesulfonylaminoquinoline-4-carboxylate (0.99 g) obtained in Reference Example 49 was hydrolyzed in the same manner as in Reference Example 48 to form 0.38 g of the above-mentioned compound.

$^1$H-NMR(DMSO-$d_6$), δ: 3.17(s,3H), 7.53–7.72(m, 4H), 7.82(d, 1H), 8.37(d, 1H), 8.45(d, 2H), 8.53(s, 1H), 9.61(s, 1H)

m.p. 263°–264° C. (decomp.)

Reference Example 51

Synthesis of 2-(2'-methoxymethyloxyphenyl)quinoline-4-carboxylic Acid

The above-mentioned compound (1.53 g) was formed from 1.47 g of isatin and 3.64 g of 2-methoxymethyloxyacetophenone in the same manner as in Reference Example 1.

$^1$H-NMR(DMSO-$d_6$), δ: 3.58(s, 3H), 5.64(s, 2H), 7.05(m, 2H), 7.51 (d, 1H), 7.60(t, 1H), 7.79(t, 1H), 7.91(m, 1h), 8.20(d, 2H), 8.70(s, 1H)

EXAMPLE 1

Synthesis of 2-phenylquinoline-4-carbonylguanidine

[A] 2-Phenyl-4-quinolinecarboxylic acid (1.99 g) and 1.43 g of 1,1'-carbonyldiimidazole were added to 20 ml of anhydrous DMF, and the mixture was stirred at room temperature for 2 hours under a nitrogen atmosphere.

[B] A mixture of 4.60 g of guanidine hydrochloride and 2.90 g of sodium methoxide was stirred in 30 ml of anhydrous methanol at room temperature for 1 hour. Then, the reaction mixture was filtered in a nitrogen stream, and the crystals were washed with methanol. The filtrate was concentrated to dryness under reduced pressure, and anhydrous benzene was added to the residue. The mixture was reconcentrated, and then dried under reduced pressure.

[C] The solution obtained in [A] was added to the dry guanidine obtained in [B] under a nitrogen atmosphere while being cooled with ice, and the mixture was stirred at room temperature for 12 hours. Subsequently, the reaction solution was concentrated under reduced pressure, and ice water was added to the residue. The mixture was further stirred for 30 minutes. The precipitate was collected by filtration, and the crystals were washed with water and then with a small amount of ethyl ether. The crystals were further washed with 10 ml of ethanol, and dried to obtain 1.85 g of the above-mentioned compound. m.p. 268° C. (decomp.)

EXAMPLE 2

Synthesis of 2-(4'-methylphenyl)quinoline-4-carbonylguanidine

The above-mentioned compound (1.35 g) was formed as a white crystal in the same manner as in Example 1 using 2.0 g of 2-(4'-methylphenyl)quinoline-4-carboxylic acid obtained in Reference Example 1 as a starting material. m.p. 244.3°–244.5° C.

EXAMPLE 3

Synthesis of 2-(3'-methylphenyl)quinoline-4-carbonylguanidine

The above-mentioned compound (0.60 g) was formed in the same manner as in Example 1 using 0.53 g of 2-(3'-methylphenyl)quinoline-4-carboxylic acid obtained in Reference Example 2 as a starting material. m.p. 248° C. (decomp.)

EXAMPLE 4

Synthesis of 2-(2'-methylphenyl)quinoline-4-carbonylguanidine

The above-mentioned compound (0.75 g) was formed in the same manner as in Example 1 using 0.79 g of 2-(2'-methylphenyl)quinoline-4-carboxylic acid obtained in Reference Example 3 as a starting material. m.p. 257.5°–258.5° C. (decomp.)

EXAMPLE 5

Synthesis of 2-(2'-isopropylphenyl)quinoline-4-carbonylguanidine

The above-mentioned compound (1.17 g) was formed as a brown crystal in the same manner as in Example 1 using 1.46 g of 2-(2'-isopropylphenyl)quinoline-4-carboxylic acid obtained in Reference Example 26 as a starting material. m.p. 224°–230° C.

EXAMPLE 6

Synthesis of 2-(2',4'-dimethylphenyl)quinoline-4-carbonylguanidine

The above-mentioned compound (1.06 g) was formed as a brown crystal in the same manner as in Example 1 using 0.96 g of 2-(2',4'-dimethylphenyl)quinoline-4-carboxylic acid obtained in Reference Example 4 as a starting material. m.p. 226°–233° C. (decomp.)

EXAMPLE 7

Synthesis of 2-(3',4'-dimethylphenyl)quinoline-4-carbonylguanidine

The above-mentioned compound (2.82 g) was formed as a white crystal in the same manner as in Example 1 using 3.3 g of 2-(3',4'-dimethylphenyl)quinoline-4-carboxylic acid obtained in Reference Example 5 as a starting material. m.p. 240°–243° C. (decomp.)

EXAMPLE 8

Synthesis of 2-(2',4',6'-trimethylphenyl)quinoline-4-carbonylguanidine

The above-mentioned compound (0.15 g) was formed in the same manner as in Example 1 using 0.14 g of 2-(2',4',6'-trimethylphenyl)quinoline-4-carboxylic acid obtained in Reference Example 6 as a starting material. m.p. 247°–250° C. (decomp.)

EXAMPLE 9

Synthesis of 2-(4'-tert-butylphenyl)quinoline-4-carbonylguanidine

The above-mentioned compound (0.69 g) was formed in the same manner as in Example 1 using 0.61 g of 2'-(4'-tert-butylphenyl)quinoline-4-carboxylic acid obtained in Reference Example 7 as a starting material. m.p. 272° C. (decomp.)

EXAMPLE 10

Synthesis of 2-(3'-trifluoromethylphenyl)quinoline-4-carbonylguanidine

The above-mentioned compound (1.30 g) was formed in the same manner as in Example 1 using 1.59 g of 2-(3'-trifluoromethylphenyl)quinoline-4-carboxylic acid obtained in Reference Example 8 as a starting material. m.p. 263° C. (decomp.)

EXAMPLE 11

Synthesis of 2-(2'-trifluoromethylphenyl)quinoline-4-carbonylguanidine

The above-mentioned compound (1.23 g) was formed in the same manner as in Example 1 using 1.59 g of 2-(2'-trifluoromethylphenyl)quinoline-4-carboxylic acid obtained in Reference Example 9 as a starting material. m.p. 251°–252° C. (decomp.)

EXAMPLE 12

Synthesis of 2-(4'-bromophenyl)quinoline-4-carbonylguanidine

The above-mentioned compound (1.40 g) was formed in the same manner as in Example 1 using 2.70 g of 2-(4'-bromophenyl)quinoline-4-carboxylic acid obtained in Reference Example 10 as a starting material. m.p. 243°–244° C. (decomp.)

EXAMPLE 13

Synthesis of 2-(4'-fluorophenyl)quinoline-4-carbonylguanidine

The above-mentioned compound (1.28 g) was formed as a white crystal in the same manner as in Example 1 using 1.70 g of 2-(4'-fluorophenyl)quinoline-4-carboxylic acid obtained in Reference Example 11 as a starting material. m.p. 238°–241° C. (decomp.)

EXAMPLE 14

Synthesis of 2-(2'-chlorophenyl)quinoline-4-carbonylguanidine

The above-mentioned compound (0.25 g) was formed in the same manner as in Example 1 using 0.83 g of 2-(2'-chlorophenyl)quinoline-4-carboxylic acid obtained in Reference Example 12 as a starting material. m.p. 250°–250.5° C. (decomp.)

EXAMPLE 15

Synthesis of 2-(4'-methoxyphenyl)quinolinecarbonylguanidine

The above-mentioned compound (1.20 g) was formed as a white crystal in the same manner as in Example 1 using 1.54 g of 2-(4'-methoxyphenyl)quinoline-4-carboxylic acid obtained in Reference Example 13 as a starting material. m.p. 244.3°–244.7° C. (decomp.)

EXAMPLE 16

Synthesis of 2-(2'-methoxyphenyl)quinoline-4-carbonylguanidine

The above-mentioned compound (0.41 g) was formed in the same manner as in Example 1 using 0.87 g of 2-(2'-methoxyphenyl)quinoline-4-carboxylic acid obtained in Reference Example 14 as a starting material. m.p. 254°–256.5° C. (decomp.)

EXAMPLE 17

Synthesis of 2-(2',6'-dimethoxyphenyl)quinoline-4-carbonylguanidine

The above-mentioned compound (20 mg) was formed in the same manner as in Example 1 using 0.52 g of 2-(2',6'-dimethoxyphenyl)quinoline-4-carboxylic acid obtained in Reference Example 15 as a starting material. m.p. 258° C. (decomp.)

EXAMPLE 18

Synthesis of 2-(4'-trifluoromethoxyphenyl)quinoline-4-carbonylguanidine

The above-mentioned compound (1.88 g) was formed in the same manner as in Example 1 using 1.67 g of 2-(4'-trifluoromethoxyphenyl)quinoline-4-carboxylic acid obtained in Reference Example 16 as a starting material. m.p. 243° C. (decomp.)

EXAMPLE 19

Synthesis of 2-(3'-nitrophenyl)quinoline-4-carbonylguanidine

The above-mentioned compound (0.76 g) was formed as a brown crystal in the same manner as in Example 1 using 0.75 g of 2-(3'-nitrophenyl)quinoline-4-carboxylic acid obtained in Reference Example 25 as a starting material. m.p. 184°–190° C.

EXAMPLE 20

Synthesis of 2-(3'-aminophenyl)quinoline-4-carbonylguanidine 2-(3'-Nitrophenyl)quinoline-4-carbonylguanidine (0.40 g) formed in Example 19 was dissolved in 40 ml of methanol, and hydrogenated under normal pressure for 5.5 hours in the presence of 0.3 g of Pd/C (purity 10%). The catalyst was filtered off from the reaction solution, and the filtrate was concentrated to obtain 0.45 g of the above-mentioned compound as a brown crystal. m.p. 209°–210° C.

EXAMPLE 21

Synthesis of 2-phenyl-3-methylquinoline-4-carbonylguanidine

The above-mentioned compound (1.06 g) was formed in the same manner as in Example 1 using 1.05 g of 2-phenyl-3-methylquinoline-4-carboxylic acid obtained in Reference Example 17 as a starting material. m.p. 270° C. or higher

EXAMPLE 22

Synthesis of 2-phenyl-6-methylquinoline-4-carbonylguanidine

The above-mentioned compound (0.52 g) was formed in the same manner as in Example 1 using 0.50 g of 2-phenyl-6-methylquinoline-4-carboxylic acid obtained in Reference Example 24 as a starting material. m.p. 276.5° C.

EXAMPLE 23

Synthesis of 2-phenyl-7-methylquinoline-4-carbonylguanidine

The above-mentioned compound (0.86 g) was formed as a pale red crystal in the same manner as in Example 1 using 0.92 g of 2-phenyl-7-methylquinoline-4-carboxylic acid obtained in Reference Example 27 as a starting material. m.p. 250° C. or higher.

EXAMPLE 24

Synthesis of 2-phenyl-8-methylquinoline-4-carbonylguanidine

The above-mentioned compound (1.50 g) was formed in the same manner as in Example 1 using 1.32 g of 2-phenyl-8-methylquinoline-4-carboxylic acid obtained in Reference Example 28 as a starting material. m.p. 221° C. (decomp.)

EXAMPLE 25

Synthesis of 2-phenyl-6-isopropylquinoline-4-carbonylguanidine

The above-mentioned compound (0.33 g) was formed in the same manner as in Example 1 using 0.98 g of 2-phenyl-6-isopropylquinoline-4-carboxylic acid obtained in Reference Example 29 as a starting material. m.p. 254.5°–255° C. (decomp.)

EXAMPLE 26

Synthesis of 2-phenyl-6-fluoroquinoline-4-carbonylguanidine

The above-mentioned compound (0.54 g) was formed in the same manner as in Example 1 using 1.07 g of 2-phenyl-6-fluoroquinoline-4-carboxylic acid obtained in Reference Example 18 as a starting material. m.p. 258° C. (decomp.)

EXAMPLE 27

Synthesis of 2-phenyl-6-iodoquinoline-4-carbonylguanidine

The above-mentioned compound (1.20 g) was formed in the same manner as in Example 1 using 1.13 g of 2-phenyl-6-iodoquinoline-4-carboxylic acid obtained in Reference Example 19 as a starting material. m.p. 270° C. or higher

EXAMPLE 28

Synthesis of 2-phenyl-5-chloroquinoline-4-carbonylguanidine

The above-mentioned compound (0.41 g) was formed as a brown crystal in the same manner as in Example 1 using 0.42 g of 2-phenyl-5-chloroquinoline-4-carboxylic acid obtained in Reference Example 20 as a starting material. m.p. 229°–234° C.

EXAMPLE 29

Synthesis of 2-phenyl-6-chloroquinoline-4-carbonylguanidine

The above-mentioned compound (1.07 g) was formed as a brown crystal in the same manner as in Example 1 using 1.0 g of 2-phenyl-6-chloroquinoline-4-carboxylic acid obtained in Reference Example 21 as a starting material. m.p. 250° C. or higher

EXAMPLE 30

Synthesis of 2-phenyl-7-chloroquinoline-4-carbonylguanidine

The above-mentioned compound (1.12 g) was formed as a brown crystal in the same manner as in Example 1 using 1.0 g of 2-phenyl-7-chloroquinoline-4-carboxylic acid obtained in Reference Example 22 as a starting material. m.p. 229°–231° C.

EXAMPLE 31

Synthesis of 2-phenyl-8-chloroquinoline-4-carbonylguanidine

The above-mentioned compound (0.11 g) was formed in the same manner as in Example 1 using 0.40 g of 2-phenyl-8-chloroquinoline-4-carboxylic acid obtained in Reference Example 30 as a starting material. m.p. 220° C. (decomp.)

EXAMPLE 32

Synthesis of 2-phenyl-6-chloro-8-methylquinoline-4-carbonylguanidine

The above-mentioned compound (1.00 g) was formed in the same manner as in Example 1 using 0.89 g of 2-phenyl-6-chloro-8-methylquinoline-4-carboxylic acid obtained in Reference Example 23 as a starting material. m.p. 159°–160° C. (decomp.)

EXAMPLE 33

Synthesis of 2-phenyl-6-methoxyquinoline-4-carbonylguanidine

The above-mentioned compound (0.68 g) was formed as a white crystal in the same manner as in Example 1 using 0.63 g of 2-phenyl-6-methoxyquinoline-4-carboxylic acid obtained in Reference Example 31 as a starting material. m.p. 250°–251° C.

EXAMPLE 34

Synthesis of 2-phenyl-7-methoxyquinoline-4-carbonylguanidine

The above-mentioned compound (1.60 g) was formed in the same manner as in Example 1 using 1.40 g of 2-phenyl-7-methoxyquinoline-4-carboxylic acid obtained in Reference Example 32 as a starting material. m.p. 263.5°–264° C.

EXAMPLE 35

Synthesis of 2-phenyl-8-methoxyquinoline-4-carbonylguanidine (Method 1)

The above-mentioned compound (2.40 g) was formed as a white crystal in the same manner as in Example 1 using 2.17 g of 2-phenyl-8-methoxyquinoline-4-carboxylic acid obtained in Reference Example 33 as a starting material.

(Method 2)

An anhydrous THF (50 ml) solution containing 4.0 g of methyl 2-phenyl-8-methoxyquinoline-4-carboxylate formed from 2-phenyl-8-methoxyquinoline-4-carboxylic acid in a usual manner was added to guanidine formed from 6.50 g of guanidine hydrochloride in the same manner as in [C] of Example 1 at room temperature. Subsequently, the mixture was heat-refluxed for 3 hours, and cooled to room temperature. The reaction mixture was then concentrated under reduced pressure, and ice water was added to the residue. The precipitate formed was collected by filtration, washed with ethyl ether, and dried to obtain 3.59 of the above-mentioned compound as a white crystal. m.p. 232°–235° C. (decomp.)

EXAMPLE 36

Synthesis of 2-phenyl-5,7-dimethoxyquinoline-4-carbonylguanidine

The above-mentioned compound (0.16 g) was formed in the same manner as in Example 1 using 0.77 g of 2-phenyl-5,7-dimethoxyquinoline-4-carboxylic acid obtained in Reference Example 34 as a starting material. m.p. 273.5° C. (decomp.)

EXAMPLE 37

Synthesis of 2-(2'-methylphenyl)-5,7-dimethoxyquinone-4-carbonylguanidine 2-(2'-Methylphenyl)-5,7-dimethoxyquinoline-4-carboxylic acid (0.80 g) formed in Reference Example 35 was suspended in 20 ml of benzene, and 1.76 g of thionyl chloride were added thereto. The mixture was heat-refluxed for 3 hours. The reaction mixture was cooled to room temperature, and then concentrated under reduced pressure. Benzene was added to the residue, and the resulting mixture was concentrated, and then dissolved in 5 ml of DMF. Guanidine formed from 0.71 g of guanidine hydrochloride was suspended in 10 ml of DMF in the same manner as in [C] of Example 1, and the above-mentioned DMF solution was added thereto dropwise at room temperature. The reaction mixture was stirred at room temperature for 1 hour, and then concentrated. Ice water was added to the residue, and the precipitate was collected by filtration to obtain crystals. The crystals were further purified through silica-gel column chromatography (mixture of methanol and chloroform at a ratio of 1:10) to form 0.29 g of the above-mentioned compound. m.p. 262°–262.5° C. (decomp.)

EXAMPLE 38

Synthesis of 2-phenyl-6,7-dimethoxyquinoline-4-carbonylguanidine

The above-mentioned compound (1.70 g) was formed in the same manner as in Example 1 using 1.60 g of 2-phenyl-6,7-dimethoxyquinoline-4-carboxylic acid obtained in Reference Example 36 as a starting material. m.p. 245° C. (decomp.)

EXAMPLE 39

Synthesis of 2-(2'-methylphenyl)-6,7-dimethoxyquinoline-4-carbonylguanidine

The above-mentioned compound (1.08 g) was formed as a white crystal in the same manner as in Example 1 using 2.57 g of 2-(2'-methylphenyl)-6,7-dimethoxyquinoline-4-carboxylic acid obtained in Reference Example 37 as a starting material. m.p. 234°–235° C.

EXAMPLE 40

Synthesis of 2-phenyl-6,8-dimethoxyquinoline-4-carbonylguanidine

The above-mentioned compound (0.21 g) was formed in the same manner as in Example 1 using 0.80 g of 2-phenyl-6,8-dimethoxyquinoline-4-carboxylic acid obtained in Reference Example 38 as a starting material. m.p. 256° C. (decomp.)

EXAMPLE 41

Synthesis of 2-(2'-methylphenyl)-6,8-dimethoxyquinoline-4-carbonylguanidine

The above-mentioned compound (1.11 g) was formed in the same manner as in Example 1 using 1.29 g of 2-(2'-methylphenyl)-6,8-dimethoxyquinoline-4-carboxylic acid obtained in Reference Example 39 as a starting material. m.p. 227°–229° C. (decomp.)

EXAMPLE 42

Synthesis of 2-(2'-methylphenyl)-5,8-dimethoxyquinoline-4-carbonylguanidine

The above-mentioned compound (0.44 g) was formed in the same manner as in Example 1 using 0.49 g of 2-(2'-methylphenyl)-5,8-dimethoxyquinoline-4-carboxylic acid obtained in Reference Example 40 as a starting material. m.p. 241° C.

EXAMPLE 43

Synthesis of 2-(2'-methylphenyl)-7,8-dimethoxyquinoline-4-carbonylguanidine

The above-mentioned compound (1.56 g) was formed as a yellow crystal in the same manner as in Example 1 using 2.20 g of 2-(2'-methylphenyl)-7,8-dimethoxyquinoline-4-carboxylic acid obtained in Reference Example 41 as a starting material. m.p. 238°14 239° C.

EXAMPLE 44

Synthesis of 2-phenyl-8-methoxyethyloxyquinoline-4-carbonylguanidine

The above-mentioned compound (1.00 g) was formed as a brown crystal in the same manner as in Example 1 using 1.30 g of 2-phenyl-8-methoxyethyloxyquinoline-4-carboxylic acid obtained in Reference Example 42 as a starting material. m.p. 218°–220° C.

EXAMPLE 45

Synthesis of 2-(2'-methylphenyl)-7-methoxymethyloxyquinoline-4-carbonylguanidine The above-mentioned compound (1.30 g) was formed as a brown crystal in the same manner as in Example 1 using 1.20 g of 2-(2'-methylphenyl)-7-methoxymethyloxyquinoline-4-carboxylic acid obtained in Reference Example 43 as a starting material. m.p. 186°–190° C.

EXAMPLE 46

Synthesis of 2-(2'-methylphenyl)-7-hydroxyquinoline-4-carbonylguanidine 2-(2'-Methylphenyl)-7-methoxymethyloxyquinoline-4-carbonylguanidine (0.9 g) formed in Example 45 was heat-stirred in 20 ml (0.5M) of an isopropyl alcohol solution of hydrochloric acid at approximately 60° C. for 3.5 hours. The reaction mixture was allowed to cool, then neutralized with a 5% sodium hydroxide aqueous solution, and concentrated. The residue was filtered, and the crystals obtained were washed with water, and dried to obtain 0.40 g of the above-mentioned compound as a brown crystal. m.p. 202°–208° C.

EXAMPLE 47

Synthesis of 2-phenyl-8-nitroquinoline-4-carbonylguanidine

The above-mentioned compound (1.07 g) was formed in the same manner as in Example 1 using 0.88 g of 2-phenyl-8-nitroquinoline-4-carboxylic acid obtained in Reference Example 45 as a starting material. m.p. 236°–236.5° C. (decomp.)

EXAMPLE 48

Synthesis of 2-phenyl-8-aminoquinoline-4-carbonylguanidine

The above-mentioned compound (0.23 g) was formed by hydrogenating 2-phenyl-8-nitroquinoline-4-carbonylguanidine obtained in Example 47 as a starting material under normal pressure in the same manner as in Example 20. m.p. 199°–200.5° C. (decomp.)

EXAMPLE 49

Synthesis of 2-phenyl-8-acetylaminoquinoline-4-carbonylguanidine

The above-mentioned compound (0.26 g) was formed in the same manner as in Example 1 using 0.31 g of 2-phenyl-8-acetylaminoquinoline-4-carboxylic acid obtained in Reference Example 48 as a starting material. m.p. 246°–246.5° C. (decomp.)

EXAMPLE 50

Synthesis of 2-phenyl-8-methanesulfonylaminoquinoline-4-carbonylguanidine

The above-mentioned compound (0.33 g) was formed in the same manner as in Example 1 using 0.31 g of 2-phenyl-8-methanesulfonylaminoquinoline-4-carboxylic acid obtained in Reference Example 50 as a starting material. m.p. 255.5°–256.0° C. (decomp.)

EXAMPLE 51

Synthesis of 2-(2'-methoxymethytoxyphenyl)quinoline-4-carbonyiguanidine

The above-mentioned compound (0.93 g) was formed in the same manner as in Example 1 using 1.43 g 2-(2'-methoxymethyloxyphenyl)quinoline-4-carboxylic acid obtained in Reference Example 51 as a starting material. m.p. 219°–220° C. (decomp.)

EXAMPLE 52

Synthesis of 2-(2'-hydroxyphenyl)quinoline-4-carbonylguanidine hydrochloride 2-(2'-Methoxymethyloxyphenyl)quinoline-4-carbonylguanidine (0.51 g) formed in Example 51 was stirred in 24 ml (5M) of an isopropyl alcohol solution of hydrochloric acid at 70° C. for 3 hours. The reaction mixture was cooled with ice, and the precipitate was collected by filtration, and dried to obtain 0.50 g of the above-mentioned compound. m.p. 270° C. or higher

EXAMPLE 53

Synthesis of 2-phenylquinoline-4-carbonylguanidine Hydrochloride

2-Phenylquinoline-4-carbonylguanidine (1.08 g) formed in Example 1 was suspended in 10 ml of ethanol, and 6 ml (1N) of an ethanol solution of hydrochloric acid were added thereto dropwise at room temperature. Thirty minutes later, ethyl ether was added to the reaction solution, and the crystals were collected by filtration, and dried to obtain 1.12 g of the above-mentioned compound. m.p. 278°–279° C. (decomp.)

EXAMPLE 54

Synthesis of 2-(2'-isopropylphenyl)quinoline-4-carbonylguanidine methanesulfonate 2-(2'-Isopropylphenyl)quinoline-4-carbonylguanidine (1.1 g) formed in Example 5 was suspended in 25 ml of ethanol, and 7.5 ml (1M) of an ethanol solution of methanesulfonic acid were added thereto dropwise while being cooled with ice. Ten minutes later, ethyl ether was added thereto, and the crystals precipitated were collected by filtration, and dried to obtain 1.10 g of the above-mentioned compound as a white crystal. m.p. 146°–154° C.

The compounds formed in Examples 1 to 51 were converted into hydrochlorides in the same manner as in Example 53 or into methanesulfonates in the same manner as in Example 54.

The analytical data of the compounds formed in Examples 1 to 52 are shown in Table 1.

TABLE 1

| Example No. | NMR (Solvent); δppm | IR (KBr, cm$^{-1}$) |
|---|---|---|
| 1 | (DMSO-$d_6$); 7.48–7.61(m, 3H), 7.76(t, 1H), 8.09(d, 1H), 8.25–8.33(m, 3H), 8.30 (s, 1H), 8.64(d, 1H) | 3377, 1593, 1524, 1380, 1314, 771 |
| 2 | (DMSO-$d_6$); 2.40(s, 3H), 7.37(d, 2H), 7.53–7.59(m, 1H), 7.72–7.78(m, 1H), 8.06(d, 1H), 8.17(d, 2H), 8.26(s, 1H), 8.60(d, 1H) | 3378, 1585, 1530, 1381, 1316, 819, 798, 760 |
| 3 | (DMSO-$d_6$); 2.38(s, 3H), 7.32(d, 1H), 7.45 (t, 1H), 7.56(t, 1H), 7.75(t, 1H), 7.99–8.09 (m, 3H), 8.28 (s, 1H), 8.63(d, 1H) | 3366, 1578, 1522, 1457, 1376, 1314 |
| 4 | (DMSO-$d_6$); 2.38(s, 3H), 7.36(m, 3H), 7.50 (m, 1H), 7.62(t, 1H), 7.79(t, 1H), 7.90(s, 1H), 8.05(d, 1H), 8.74(d, 1H) | 3449, 1654, 1608, 1523, 1457, 1374, 1308, 769 |
| 5 | (DMSO-$d_6$); 1.17(d, 6H), 3.11–3.24(m, 1H), 7.31–7.78(m, 6H), 7.83(s, 1H), 8.02(d, 1H), 8.30(s, 4H), 8.75(d, 1H) | 3449, 1654, 1609, 1523, 1375, 1306, 1063, 811, 763 |
| 6 | (DMSO-$d_6$); 2.37(s, 6H), 7.16(d, 2H), 7.39 (d, 1H), 7.60(t, 1H), 7.76(t, 1H), 7.84(s, 1H), 8.04(d, 1H), 8.27(s, 4H), 8.68(d, 1H) | 3447, 2975, 1649, 1578, 1517, 1365, 1303, 1091, 1050, 897, 882, 810, 767 |
| 7 | (DMSO-$d_6$); 2.31(s, 3H), 2.36 (s, 3H), 7.31 (d, 1H), 7.55(t, 1H), 7.70–7.76(m, 1H), 7.96–8.07(m, 2H), 8.25(s, 1H), 8.31(s, 4H), 8.60 (d, 1H) | 3376, 1584, 1541, 1457, 1374, 758 |
| 8 | (DMSO-$d_6$); 1.95(s, 6H), 2.31(s, 3H), 6.98 (s, 2H), 7.48–7.64(m, 2H), 7.76(t, 1H), 8.02(d, 1H), 8.26(s, 4H), 8.72(d, 1H) | 3422, 1637, 1578, 1560, 1522, 1457 |
| 9 | (DMSO-$d_6$); 1.35(s, 9H), 7.57(d, 3H), 7.74 (t, 1H), 8.06(d, 1H), 8.18(d, 2H), 8.25(s, 1H), 8.60–8.63 (m, 1H) | 3447, 2963, 1610, 1523, 1377, 1314, 766 |
| 10 | (DMSO-$d_6$); 7.65(t, 1H), 7.82(m, 3H), 8.16 (d, 1H), 8.36 (s, 1H), 8.57 (m, 3H) | 3368, 1583, 1523, 1437, 1384, 1341, 1233, 1168, 1126, 1073, 888, 800, 758 698 |
| 11 | (DMSO-$d_6$); 7.70 (m, 4H), 7.85 (m, 2H), 7.92 (d, 1H), 8.06(d, 1H), 8.69(d, 1H) | 3422, 1617, 1522, 1375, 1316, 1174, 1128, 771 |
| 12 | (DMSO-$d_6$); 6.96(br s, 1H), 7.60(m, 1H), 7.76(d, 2H), 8.08(d, 1H), 8.24(d, 2H), 8.29 (s, 1H), 8.61(d, 2H) | 3371, 1584, 1529, 1399, 1378, 1312, 1076, 1009, 759 |
| 13 | DMSO-$d_6$); 7.38(t, 2H), 7.58–7.62(m, 1H), 7.74–7.80(m, 1H), 8.08(d, 1H), 8.25–8.34 (m, 3H), 8.60(d, 1H) | 3394, 1579, 1517, 1382, 1315, 1234, 841, 812, 760 |
| 14 | (DMSO-$d_6$); 7.12(t, 1H), 7.19(d, 1H), 7.47 (t, 1H), 7.57(d.1H).7.75(m, 2H), 8.05(d, 1H), 8.12(s, 1H), 8.31(s, 4H), 8.65(d, 1H) | 3445, 1602, 1525, 1460, 1375, 1312, 1247, 1025, 759 |
| 15 | (DMSO-$d_6$); 3.86(s, 3H), 7.12(d, 2H), 7.53–7.59(m, 1H), 7.72–7.78(m, 1H), 8.06(d, 1H), 8.20(s, 1H), 8.22(d, 2H), 8.55(d, 1H) | 3367, 1585, 1522, 1380, 1180, 1027, 833, 800, 759 |
| 16 | (DMSO-$d_6$); 3.54(s, 3H), 7.12(t, 1H), 7.20 (d, 1H), 7.49(t, 1H), 7.59(t, 1H), 7.76(m, 2H), 8.06(d, 1H), 8.10(s, 1H), 8.63(d, 1H) | 3855, 1602, 1524, 1459, 1374, 1312, 1247, 1025, 758 |
| 17 The 2CH$_3$SO$_3$H salt was measured. | (DMSO-$d_6$); 2.39(s, 6H), 3.71(s, 6H), 6.85 (s, 1H), 6.88(s, 1H), 7.51(t, 1H), 7.86(t, (s, 1H), 6.88(s, 1H), 7.51(t, 1H), 7.86(t, 1H), 7.88(s, 1H), 7.97(t, 1H), 8.18(d, 1H), 8.30(d, 1H) | 3380, 3108, 1722, 1598, 1234, 1112, 1043, 785 |
| 18 | (DMSO-$d_6$); 7.58(m, 3H), 7.79(t, 1H), 8.10 (d, 1H), 8.31(s, 1H), 8.38(d, 2H), 8.63(d, 1H) | 3381, 1585, 1522, 1378, 1258 |
| 19 | (DMSO-$d_6$); 7.61–7.64(m, 1H), 7.81–7.90 (m, 2H), 8.13(d, 1H), 8.31(s, 4H), 8.34–8.40 (m, 2H), 8.63–8.73(m, 2H), 9.07–9.08(m, 1H) | 3374, 1653, 1526, 1349, 809, 696 |
| 20 | (DMSO-$d_6$); 6.68–6.71(m, 1H), 7.14–7.36(m, 2H), 7.51–7.58(m, 2H), 7.71–7.76(m, 1H), 8.03 (d, 1H), 8.18 (s, 1H), 8.31 (s, 4H), 8.63 (d, 1H) | 3378, 1583, 1380, 882 |
| 21 | (DMSO-$d_6$); 2.30(s, 3H), 7.52(m, 6H), 7.65 (m, 1H), 7.90(m, 2H) | 3855, 3056, 1671, 1560, 1396, 1334, 767 |
| 22 | (DMSO-$d_6$); 3.32(s, 3H), 7.51(m, 4H), 7.99 (d, 1H), 8.25(m, 3H), 8.39(s, 1H) | 3369, 1654, 1541, 1508, 1457, 1378, 1318 |

TABLE 1-continued

| Example No. | NMR (Solvent); δppm | IR (KBr, cm$^{-1}$) |
|---|---|---|
| 23 | (DMSO-d$_6$); 7.43–7.61(m, 4H), 7.90(s, 1H), 8.19–8.23(m, 3fl), 8.50(d, 1H) | 3376, 1655, 1592, 1524, 1457, 1375, 1316, 1069, 886, 826, 769, 701, 669 |
| 24 | (DMSO-d$_6$); 2.83(s, 3H), 7.57(m, 5H), 8.27 (m, 3H), 8.39 (d, 1H) | 3451, 3365, 1656, 1587, 1559, 1523, 1373, 1317, 763 |
| 25 | (DMSO-d$_6$); 1.32(d, 6H), 3.12(m, 1H), 7.56 (m, 3H), 7.72(m, 1H ), 8.01 (d, 1H), 8.25(m, 2H), 8.27(s, 1H), 8.45(m, 1H) | 3455, 3326, 2962, 1653, 1602, 1518, 1372, 1315, 769, 705 |
| 26 | (DMSO-d$_6$); 7.58(m, 3H), 7.71(m, 1H), 8.17 (m, 1H), 8.26(d, 2H), 8.48(s, 1H), 8.59(m, 1H | 3381, 1577, 1552, 1363, 1318, 1236, 835, 703 |
| 27 | (DMSO-d$_6$); 7.57(m, 2H), 7.90(d, 1H), 8.03 (m, 1H), 8.22 (s, 1H), 8.25 (m, 2H), 8.35 (s, 1H).9.08(m, 1H) | 3375, 1595, 1541, 1457, 1390, 1317 |
| 28 | (DMSO-d$_6$); 7.53–7.76(m, 6H), 7.92(s, 1H), 8.06 (d, 1H), 8.30(s, 4H), 8.30–8.36 (m, 1H) | 3448, 1654, 1596, 1522, 1457, 1362, 1311, 1197, 1071, 777, 698 |
| 29 | (DMSO-d$_6$);7.50–7.62(m, 3H), 7.76–7.80(m, 1H), 8.12(d, 1H), 8.25(d, 2H), 8.43(s, 1H), 8.80(s, 1H) | 3378, 1590, 1530, 1492, 1453, 1397, 1378, 1317, 1065, 887, 826, 758, 702 |
| 30 | (DMSO-d$_6$); 7.52–7.63(m, 4H), 8.12(s, 1H), 8.24–8.31 (m, 2H), 8.31(s, 4H), 8.36(s, 4H), 8.75(d, 1H) | 3376, 1600, 1523, 1374, 1316, 1083, 908, 829, 767 |
| 31 | (DMSO-d$_6$); 7.56(m, 4H), 7.95(d, 1H), 8.35 (m, 3H), 8.58(d, 1H) | 3453, 1599, 1521, 1374, 1314, 1063, 824, 750, 699 |
| 32 | (DMSO-d$_6$); 2.83(s, 3H), 7.59(m, 2H), 7.65 (m, 1H ), 8.21(s, 1H), 8.29(m, 2H), 8.37(s, 1H), 8.53(m, 1H) | 3386, 1579, 1522, 1452, 1375, 1320, 884, 767, 706 |
| 33 | (DMSO-d$_6$); 3.91(s, 3H), 7.40–7.58 (m, 4H), 8.01(d, 1H), 8.19–8.27(m, 3H), 8.35(s, 1H), 8.30(s, 4H) | 3322, 1655, 1624, 1578, 1523, 1355, 1314, 1229, 831 |
| 34 | (DMSO-d$_6$); 3.96(s, 3H), 7.27(d, 1H), 7.58 (m, 4H), 8.14(s, 1H), 8.23(d, 2H), 8.53(d, 1H) | 3370, 1619, 1518, 1376, 1315 |
| 35 | (DMSO-d$_6$); 4.02(s, 3H), 7.19(d.1H), 7.44–7.58(m, 4H), 8.09(d, 1H), 8.23–8.30(m, 3H), 8.37(s, 4H) | 3380, 1662, 1608, 1526, 1364, 1316, 1262, 754 |
| 36 | (DMSO-d$_6$); 3.81(s, 3H), 3.93(s, 3H), 6.60 (s, 1H), 7.06(s, 1H), 7.41 (m, 3H), 7.52(s, 1H), 8.22(d, 2H) | 3373, 1620, 1599, 1518, 1371, 1314, 1254, 1209, 1167, 1141 |
| 37 | (DMSO-d$_6$); 2.35(s, 3H), 3.81(s, 3H), 3.90 (s, 3H), 6.63(d, 1H) 7.00(d, 1H), 7.04(s, 1H), 7.33(m, 4H) | 3448, 1619, 1519, 1457, 1367, 1308, 1252, 1209, 1143 |
| 38 | (DMSO-d$_6$); 3.98(s, 3H), 4.04(s, 3H), 7.46–7.57(m, 4H), 8.19–8.28(m, 4H) | 3855, 1637, 1508, 1375, 1250 |
| 39 | (DMSO-d$_6$); 2.37(s, 3H), 3.92(s, 3H), 3.94 (s, 3H), 7.27–7.46 (m, 5H), 7.85 (s, 1H), 8.36 (s, 1H) | 3442, 1654, 1508, 1357, 1249, 1162, 1043, 858, 764 |
| 40 | (DMSO-d$_6$); 3.93(s, 3H), 3.99(s, 3H), 6.85 (d, 1H), 7.45–7.59(3m, H), 7.72(d, 1H), 8.18–8.23(m, 2H), 8.28(s, 1H) | 3450, 1619, 1522, 1363, 1324, 1217, 1155, 768 |
| 41 | (DMSO-d$_6$); 2.35(s, 3H), 3.88(s, 3H), 3.94 (s, 3H), 6.83 (d, 1H), 7.28–7.44 (m, 4H), 7.80 (d, 1H), 7.9 1 (s, 1H) | 3422, 1619, 1523, 1457, 1374, 1216, 1155, 755 |
| 42 | (DMSO-d$_6$); 2.35(s, 3H), 3.79(s, 3H), 3.90 (s, 3H), 6.92(d, 1H), 7.11(d, 1H), 7.25(s, 1H), 7.37(m, 4H), 8.37(s, 4H) | 3444, 1614, 1526, 1470, 1367, 1311, 1261, 1105, 761 |
| 43 | (DMSO-d$_6$); 2.41(s, 3H), 3.94(s, 3H), 3.98 (s, 3H), 7.34–7.36(m, 3H), 7.48–7.54(m, 2H) 7.73(s, 1H), 8.45(d, 1H) | 3446, 1653, 1605, 1513, 1459, 1355, 1306, 1268, 1105, 740 |
| 44 | (DMSO-d$_6$); 3.41(s, 3H), 3.75(t, 2H), 4.26 (t, 2H), 7.13(d, 1H), 7.29–7.54(m, 4H), 7.98 (d, 1H), 8.01–8.27(m, 3H) | 3448, 1655, 1606, 1534, 1458, 1372, 1318, 1262, 1100, 824, 756, 703 |
| 45 | (DMSO-d$_6$); 2.37(s, 3H), 3.44(s, 3H), 5.38 (s, 2H), 7.30–7.63 (m, 6H), 7.76 (s, 1H), 8.31 (s, 4H), 8.70(d, 1H) | 3424, 1594, 1515, 1377, 1311, 1149, 1081, 1067, 992, 832, 770, 750, 661 |
| 46 | (DMSO-d$_6$); 2.38(s, 3H), 7.18–7.50(m, 6H), | 3383, 2975, 1622, |

TABLE 1-continued

| Example No. | NMR (Solvent); δppm | IR (KBr, cm$^{-1}$) |
| --- | --- | --- |
|  | 7.67(s, 1H), 8.53(d, 1H) | 1522, 1457, 1387, 1231, 1090, 882, 746 |
| 47 | (DMSO-d$_6$); 7.61(m, 3H), 7.75(t, 1H), 8.28 (m, 3H), 8.53(s, 1H), 8.97(d, 1H) | 3398, 1671, 1589, 1527, 1355, 1314, 765 |
| 48 | (D$_2$O); 6.88(d, 1H), 7.27(t, 1H), 7.55 (m, 3H), 7.63 ( d, 1H), 8.17(s, 1H), 8.31(d, 2H) | 3367, 1616, 1522, 1466, 1376, 1323, 766 |
| 49 | (DMSO-d$_6$); 3.34(s, 3H), 7.58(m, 4H), 7.75 (d, 1H), 8.36(m, 3H), 9.50(s, 1H) | 3409, 1606, 1555, 1528, 1465, 1376, 1319, 1150 |
| 50 | (DMSO-d$_6$); 2.34(s, 3H), 7.60(m, 4H), 8.23 (d, 1H), 8.32(s, 1H), 8.40(m, 2H), 8.59(d, 1H) | 3340, 1670, 1586, 1531, 1374, 1324, 765, 693 |
| 51 | (DMSO-d$_6$); 3.34(s, 3H), 5.27(s, 2H), 7.18 (t, 1H), 7.29(d, 1H), 7.45(t, 1H), 7.60(t, 1H), 7.73–7.81(m, 2H), 8.08(d, 1H), 8.20(s, 1H), 8.70(d, 1H) | 3449, 1603, 1524, 1376, 1310, 990, 764 |
| 52 The HCl salt was measured. | (DMSO-d$_6$); 7.03–7.09(m, 2H), 7.44–7.50(m, 1H), 7.77–7.82(m, 1H), 7.93–7.99(m, 1H), 8.21–8.33(m, 3H), 8.74(s, 1H) | 3375, 2854, 1717, 1607, 1571, 1508, 1237, 768 |

Preparation Example 1

Oral Agent Containing 2-phenyl-8-methoxyquinoline-4-carbonylguanidine (Example 35) Methanesulfonate as an Active Ingredient Ninety grams of the compound of the present invention were mixed with 40 g of lactose. The mixture was sieved through a No. 60 screen, and was wet-granulated with an alcohol solution containing 15 g of polyvinyl pyrrolidone. Then, 30 g of corn starch were added thereto, and these were mixed until uniform particles were formed. The mixture was passed through a No. 10 screen, placed on a tray, and dried in an oven of 60° C. for 12 hours. The thus-dried particles were sieved through a No. 16 screen, and mixed with 3 g of magnesium stearate. The mixture was formed into tablets 7 mm in diameter by means of a tablet making machine through compression. The tablets were treated with varnish, and talc was spread. Then, moisture absorption was prevented, and an undercoat layer was coated around the cores. Varnish coating was conducted for internal use. In order to make the tablets completely smooth, an undercoat layer and a smooth coating were further applied thereto. The thus-coated tablets were dried, and then polished to form uniform glossy tablets.

Preparation Example 2

Oral Agent Containing 2-(2'-methylphenyl)-5,7-dimethoxyquinoline-4-carbonylguanidine (Example 37) Methanesulfonate as an Active Ingredient A tablet was prepared from 80 g of the compound of the present invention, 40 g of lactose, 13 g of polyvinyl pyrrolidone, 30 g of corn starch and 3 g of magnesium stearate in the same manner as in Preparation Example 1.

Preparation Example 3

Injection Containing 2-(2'-methylphenyl)-5,8-dimethoxyquinoline-4-carbonylguanidine (Example 42) Methanesulfonate as an Active Ingredient The compound (0.5 g) of the present invention was taken up, and dissolved in 10 ml of a 0.9% physiological saline solution. The mixture was sterilized through filtration, and poured into a 10-milliliter ampoule to form an injection.

Preparation Example 4

Injection containing 2-phenyl-5,7-dimethoxyquinoline-4-carbonylguanidine (Example 36) Hydrochloride as an Active Ingredient An injection was prepared from 0.3 g of the compound of the present invention and 10 ml of a 0.9% physiological saline solution in the same manner as in Preparation Example 3.

Test Example 1

NHE Inhibitory Activity

The NHE inhibitory activity was measured by the following method using a pH in cells as an index.

[Method of measuring a pH in cells]

A rat mesenteric artery was isolated, and was loaded with a pH-sensitive dye BCECF. Subsequently, the tissue segments were mounted in a bath of an intracellular ion concentration measurement device (CAF-110, manufactured by Japan Spectral Co., Ltd.). The pH in cells was measured in terms of a ratio of fluorescent intensities through 2-wavelength excitation of 495 nm (pH-sensitive wavelength)/450 nm (pH-non-sensitive wavelength).

[Measurement of the NHE activity]

The pH in cells was shifted into acid through pretreatment with 20 mM ammonium chloride to activate NHE. At this time, when Na$^+$ ions were absent in an external solution, the intracellular acidosis was maintained. When Na$^+$ ions were present in an external solution, the pH in cells was recovered to a control value. This recovery of the pH in cells was ascribable to the activation of NHE. The NHE inhibitory activity of the medication was examined depending on whether or not this recovery was suppressed. The percent NHE inhibition was calculated from a change in pH (ΔpH) measured by the above-mentioned method using the following formula.

Percent NHE inhibition (%)={1−ΔpH (in the presence of a medication)/ΔpH (in the absence of a medication)}×100

This test was conducted by the method of C. D. Foster et al. [Am. J. Physiol., 262, 31, H1651–H1655 (1992)]. For comparison, the test was conducted with respect to guanidinocarbonylisoquinoline derivatives described in JP A 6-211799 (Family: EP590455). The results of the measurements are shown in Table 2.

TABLE 2

| | Inhibitory effect on NHE activity | |
|---|---|---|
| | Percent NHE inhibition (%) Conc. (µM) | |
| Example No.: Test Compound | 0.1 | 1 |
| 2-(2'-methylphenyl)-4-guadininocarbonyl-1(2H)-isoquinoline hydrochloride (control compound) | | |
| 1: 2-phenylquinoline-4-carbonylguanidine hydrochloride | 5.2 | 52.8 |
| 2: 2-(4'-methylphenyl)quinoline-4-carbonylguanidine hydrochloride | 10.6 | 41.4 |
| 3: 2-(3'-methylphenyl)quinoline-4-carbonylguanidine hydrochloride | 21.2 | 59.8 |
| 4: 2-(2'-methylphenyl)quinoline-4-carbonylguanidine hydrochloride | 49.2 | 65.6 |
| 5: 2-(2'-isopropylphenyl)quinoline-4-carbonylguanidine methanesulfonate | 29.3 | 42.3 |
| 6: 2-(2',4'-dimethylphenyl)quinoline-4-carbonylguanidine methanesulfonate | 36.4 | 55.3 |
| 7: 2-(3',4'-dimethylphenyl)quinoline-4-carbonylguanidine methanesulfonate | 33.1 | 38.8 |
| 8: 2-(2',4',6'-trimethylphenyl)quinoline-4-carbonylguanidine methanesulfonate | 23.7 | 36.3 |
| 11: 2-(2'-trifluoromethylphenyl)quinoline-4-carbonylguanidine methanesulfonate | 22.7 | 46.1 |
| 13: 2-(4'-fluorophenyl)quinoline-4-carbonylguanidine hydrochloride | 14.4 | 39.8 |
| 14: 2-(2'-chlorophenyl)quinoline-4-carbonylguanidine methanesulfonate | 28.8 | 34.3 |
| 19: 2-(3'-nitrophenyl)quinoline-4-carbonylguanidine hydrochloride | 22.3 | 35.6 |
| 20: 2-(3'-aminophenyl)quinoline-4-carbonylguanidine hydrochloride | 36.2 | 42.2 |
| 21: 2-phenyl-3-methylquinoline-4-carbonylguanidine methanesulfonate | 1.5 | 45.0 |
| 22: 2-phenyl-6-methylquinoline-4-carbonylguanidine methanesulfonate | 28.9 | 57.9 |
| 23: 2-phenyl-7-methylquinoline-4-carbonylguanidine methanesulfonate | 2.8 | 49.8 |
| 24: 2-phenyl-8-methylquinoline-4-carbonylguanidine methanesulfonate | 8.1 | 50.0 |
| 28: 2-phenyl-5-chloroquinoline-4-carbonylguanidine methanesulfonate | 33.7 | 63.3 |
| 29: 2-phenyl-6-chloroquinoline-4-carbonylguanidine methanesulfonate | 0 | 38.6 |
| 31: 2-phenyl-8-chloroquinoline-4-carbonylguanidine methanesulfonate | 12.0 | 57.0 |
| 32: 2-phenyl-6-chloro-8-methylquinoline-4-carbonylguanidine hydrochloride | 28.6 | 35.7 |
| 34: 2-phenyl-7-methoxyquinoline-4-carbonylguanidine methanesulfonate | 29.8 | 53.0 |
| 35: 2-phenyl-8-methoxyquinoline-4-carbonylguanidine methanesulfonate | 47.4 | 63.6 |
| 36: 2-phenyl-5,7-dimethoxyquinoline-4-carbonylguanidine hydrochloride | 53.2 | 69.9 |
| 37: 2-(2'-methylphenyl)-5,7-dimethoxyquinoline-4-carbonylguanidine methanesulfonate | 70.8 | 84.2 |
| 39: 2-(2'-methylphenyl)-6,7-dimethoxyquinoline-4-carbonylguanidine methanesulfonate | 3.4 | 41.5 |
| 40: 2-phenyl-6,8-dimethoxyquinoline-4-carbonylguanidine methanesulfonate | 18.3 | 31.0 |
| 42: 2-(2'-methylphenyl)-5,8-dimethoxyquinoline-4-carbonylguanidine methanesulfonate | 72.7 | 89.1 |
| 43: 2-(2'-methylphenyl)-7,8-dimethoxyquinoline-4-carbonylguanidine methanesulfonate | 28.0 | 37.6 |

TABLE 2-continued

| | Inhibitory effect on NHE activity | |
|---|---|---|
| | Percent NHE inhibition (%) Conc. (µM) | |
| Example No.: Test Compound | 0.1 | 1 |
| 44: 2-phenyl-8-methoxyethyloxyquinoline-4-carbonylguanidine methanesulfonate | 28.4 | 62.9 |
| 45: 2-(2'-methylphenyl)-7-methoxymethyloxyquinoline-4-carbonylguanidine methanesulfonate | 35.0 | 46.5 |
| 46: 2-(2'-methylphenyl)-7-hydroxyquinoline-4-carbonylguanidine methanesulfonate | 39.3 | 48.8 |
| 48: 2-phenyl-8-aminoquinoline-4-carbonylguanidine methanesulfonate | 30.6 | 41.7 |
| 49: 2-phenyl-8-acetylaminoquinoline-4-carbonylguanidine methanesulfonate | 20.8 | 51.2 |
| 50: 2-phenyl-8-methanesulfonylaminoquinoline-4-carbonylguanidine methanesulfonate | 46.2 | 66.2 |

Test Example 2

Effect on Ischemic Arrhythmia in the Rat

A rat was anesthetized with pentobarbital, and the left chest was opened under artificial respiration. Then, the left coronary artery was ligated for 30 minutes. The effect of the test compound on ischemic arrhythmia was examined. The test agent was administered intravenously (i.v.) five minutes before the ligation. The arrhythmias were evaluated according to the guidelines of the Lambeth conventions [Cardiovasc. Res., 22, 447–455 (1988)]. The test compounds, the number of examples and the number of rats in which the arrhythmia occurred are shown in Table 3.

TABLE 3

| | Effect on ischemic arrhythmia (i.v.) | | |
|---|---|---|---|
| | | Incidence of arrhythmia | |
| Example No.: Test Compound | Number of examples | VT | VF |
| physiological saline (control) | 11 | 5/5 | 4/5 |
| 36: 2-phenyl-5,7-dimethoxyquinoline-4-carbonylguanidine hydrochloride (1 mg/kg) | 4 | 2/4 | 0/4 |
| 37: 2-(2'-methylphenyl)-5,7-dimethoxyquinoline-4-carbonylguanidine methanesulfonate (1 mg/kg) | 5 | 3/5 | 0/5 |
| 42: 2-(2'-methylphenyl)-5,8-dimethoxyquinoline-4-carbonylguanidine methanesulfonate (1 mg/kg) | 4 | 2/4 | 0/4 |

VT: ventricular tachycardia
VF: ventricular fibrillation

Test Example 3

Toxicity Test

The test compound was administered to a ddy-strain male mouse, and the toxicity was examined. The test compound was administered intravenously (i.v.) in a dose of 100 mg/kg, and the toxicity was evaluated in terms of mortality of mice after 24 hours of the administration (number of specimens: one group consisting of 3 mice). The results are shown in Table 4.

TABLE 4

Result of toxicity test

| Example No.: Test Compound | Mortality (%) 100 mg/kg (i.v.) |
|---|---|
| 42: 2-(2'-methylphenyl)-5,8-dimethoxyquinoline-4-carbonylguanidine methanesulfonate | 0 |

As mentioned above, the compounds of the present invention have a strong inhibitory effect on NHE activity, and these compounds are quite useful as an agent for preventing or treating diseases caused by enhanced NHE activity, such as hypertension, arrhythmia, myocardial infarction, angina pectoris, arteriosclerosis, diabetic complication, cancers, fibrosis, cardiac hypertrophy, prostatic hypertrophy and the like. Further, these compounds are useful as an ingredient of a protective solution of internal organs cut from the body for transplantation or internal organs transplanted and as a diagnostic agent for diseases in which NHE activity is enhanced.

What we claim is:

1. A quinoline-4-carbonylguanidine derivative represented by formula (1)

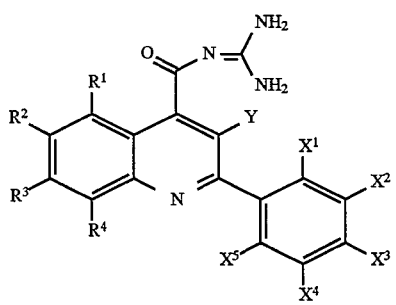

wherein $R^1$, $R^2$, $R^3$ and $R^4$ are the same or different and each represents a hydrogen atom, an alkyl group having from 1 to 6 carbon atoms, a halogen atom, a nitro group, an amino group, a hydroxyl group, an alkyloxy group having from 1 to 6 carbon atoms, an alkyloxy group having from 1 to 6 carbon atoms and containing a terminal alkyloxy group having from 1 to 6 carbon atoms, an alkylsulfonylamino group having from 1 to 6 carbon atoms, or an alkanoylamino group having from 2 to 6 carbon atoms, $X^1$, $X^2$, $X^3$, $X^4$ and $X^5$ are the same or different and each represents a hydrogen atom, an alkyl group having from 1 to 6 carbon atoms, a halogen atom, a nitro group, an amino group, a hydroxyl group, a trifluoromethyl group, an alkyloxy group having from 1 to 6 carbon atoms, an alkyloxy group having from 1 to 6 carbon atoms and containing a terminal alkyloxy group having from 1 to 6 carbon atoms, or a trifluoromethoxy group, and Y represents a hydrogen atom, or an alkyl group having from 1 to 6 carbon atoms, or a pharmaceutically acceptable salt thereof.

2. The quinoline-4-carbonylguanidine derivative or the pharmaceutically acceptable salt thereof as mentioned in claim 1, wherein one or two of $R^1$, $R^2$, $R^3$ and $R^4$ represent an alkyloxy group having from 1 to 6 carbon atoms.

3. The quinoline-4-carbonylguanidine derivative or the pharmaceutically acceptable salt thereof as mentioned in claim 1, wherein $X^1$ represents a methyl group.

4. The quinoline-4-carbonylguanidine derivative or the pharmaceutically acceptable salt thereof as mentioned in claim 2, wherein $X^1$ represents a methyl group.

5. A process for producing the quinoline-4-carbonylguanidine derivative of claim 1, which comprises reacting a quinoline-4-carboxylic acid derivative represented by formula (2)

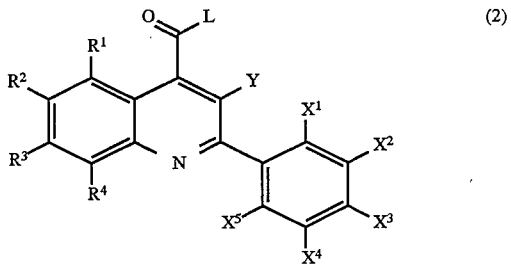

wherein

L represents a hydroxyl group, or a leaving group that can easily be substituted by means of a nucleophilic reagent, and $R^1$, $R^2$, $R^3$, $R^4$, $X^1$, $X^2$, $X^3$, $X^4$, $X^5$ and Y are as defined in formula (1)

with guanidine.

6. A pharmaceutical composition containing as an active ingredient the quinoline-4-carbonylguanidine derivative or the pharmaceutically acceptable salt thereof as mentioned in claim 4.

7. A $Na^+/H^+$ exchanger inhibitor containing as an active ingredient the quinoline-4-carbonylguanidine derivative or the pharmaceutically acceptable salt thereof as mentioned in claim 4.

8. An agent for treating or preventing hypertension, said agent containing as an active ingredient the quinoline-4-carbonylguanidine derivative or the pharmaceutically acceptable salt thereof as mentioned in claim 1.

9. An agent for treating or preventing arrhythmia, said agent containing as an active ingredient the quinoline-4-carbonylguanidine derivative or the pharmaceutically acceptable salt thereof as mentioned in claim 4.

10. An agent for treating or preventing angina pectoris, reperfusion arrhythmia and myocardial infarction caused by ischemia, ischemic arrhythmia, organ disorders caused by ischemia and reperfusion, cerebral ischemic disorders, cerebral apoplexy and ischemic diseases of limbs and peripheral organs, said agent containing as an active ingredient the quinoline-4-carbonylguanidine derivative or the pharmaceutically acceptable salt thereof as mentioned in claim 4.

11. An agent for treating or preventing diseases caused by cell proliferation or hypertrophy, said agent containing as an active ingredient the quinoline-4-carbonylguanidine derivative or the pharmaceutically acceptable salt thereof as mentioned in claim 1.

12. An agent for treating or preventing organ disorders caused by ischemia in a surgical operation or transplantation of internal organs, said agent containing as an active ingredient the quinoline-4-carbonylguanidine derivative or the pharmaceutically acceptable salt thereof as mentioned in claim i.

13. An agent for treating or preventing diseases caused by infiltration of leukocytes, said agent containing as an active ingredient the quinoline-4-carbonylguanidine derivative or the pharmaceutically acceptable salt thereof as mentioned in claim 1.

14. A protective solution for internal organs cut from the body for transplantation or internal organs transplanted, said protective solution containing as an active ingredient the quinoline-4-carbonylguanidine derivative or the pharmaceutically acceptable salt thereof as mentioned in claim 1.

15. An agent for diagnosis of hypertension, diseases caused by cell growth and diabetes through inhibition of a $Na^+/H^{30}$ exchanger, said agent containing as an active ingredient the quinoline-4-carbonylguanidine derivative or the pharmaceutically acceptable salt thereof as mentioned in claim 1.

16. A pharmaceutical composition containing as an active ingredient the quinoline-4-carbonylguanidine derivative or the pharmaceutically acceptable salt thereof as mentioned in claim 3.

17. A pharmaceutical composition containing as an active ingredient the quinoline-4-carbonylguanidine derivative or the pharmaceutically acceptable salt thereof as mentioned in claim 2.

18. A pharmaceutical composition containing as an active ingredient the quinoline-4-carbonylguanidine derivative or the pharmaceutically acceptable salt thereof as mentioned in claim 1.

19. A $Na^+/H^+$ exchanger inhibitor containing as an active ingredient the quinoline-4-carbonylguanidine derivative or the pharmaceutically acceptable salt thereof as mentioned in claim 3.

20. A $Na^+/H^+$ exchanger inhibitor containing as an active ingredient the quinoline-4-carbonylguanidine derivative or the pharmaceutically acceptable salt thereof as mentioned in claim 2.

21. A $Na^+/H^+$ exchanger inhibitor containing as an active ingredient the quinoline-4-carbonylguanidine derivative or the pharmaceutically acceptable salt thereof as mentioned in claim 1.

22. An agent for treating or preventing arrhythmia, said agent containing as an active ingredient the quinoline-4-carbonylguanidine derivative or the pharmaceutically acceptable salt thereof as mentioned in claim 3.

23. An agent for treating or preventing arrhythmia, said agent containing as an active ingredient the quinoline-4-carbonylguanidine derivative or the pharmaceutically acceptable salt thereof as mentioned in claim 2.

24. An agent for treating or preventing arrhythmia, said agent containing as an active ingredient the quinoline-4-carbonylguanidine derivative or the pharmaceutically acceptable salt thereof as mentioned in claim 1.

25. An agent for treating or preventing angina pectoris, reperfusion arrhythmia and myocardial infarction caused by ischemia, ischemic arrhythmia, organ disorders caused by ischemia and reperfusion, cerebral ischemic disorders, cerebral apoplexy and ischemic diseases or limbs and peripheral organs, said agent containing as an active ingredient the quinoline-4-carbonylguanidine derivative or the pharmaceutically acceptable salt thereof as mentioned in claim 3.

26. An agent for treating or preventing angina pectoris, reperfusion arrhythmia and myocardial infarction caused by ischemia, ischemic arrhythmia, organ disorders caused by ischemia and reperfusion, cerebral ischemic disorders, cerebral apoplexy and ischemic diseases or limbs and peripheral organs, said agent containing as an active ingredient the quinoline-4-carbonylguanidine derivative or the pharmaceutically acceptable salt thereof as mentioned in claim 2.

27. An agent for treating or preventing angina pectoris, reperfusion arrhythmia and myocardial infarction caused by ischemia, ischemic arrhythmia, organ disorders caused by ischemia and reperfusion, cerebral ischemic disorders, cerebral apoplexy and ischemic diseases or limbs and peripheral organs, said agent containing as an active ingredient the quinoline-4-carbonylguanidine derivative or the pharmaceutically acceptable salt thereof as mentioned in claim 1.

* * * * *